(12) United States Patent
Salisbury, Jr. et al.

(10) Patent No.: US 6,522,906 B1
(45) Date of Patent: Feb. 18, 2003

(54) DEVICES AND METHODS FOR PRESENTING AND REGULATING AUXILIARY INFORMATION ON AN IMAGE DISPLAY OF A TELESURGICAL SYSTEM TO ASSIST AN OPERATOR IN PERFORMING A SURGICAL PROCEDURE

(75) Inventors: J. Kenneth Salisbury, Jr., Atherton, CA (US); Gunter D. Niemeyer, Mountain View, CA (US); Robert G. Younge, Portola Valley, CA (US); Gary S. Guthart, Foster City, CA (US); David S. Mintz, Sunnyvale, CA (US); Thomas G. Cooper, Menlo Park, CA (US)

(73) Assignee: Intuitive Surgical, Inc., Mountain View, CA (US)

( * ) Notice: Subject to any disclaimer, the term of this patent is extended or adjusted under 35 U.S.C. 154(b) by 0 days.

(21) Appl. No.: 09/464,455

(22) Filed: Dec. 14, 1999

Related U.S. Application Data

(63) Continuation-in-part of application No. 09/457,406, filed on Dec. 7, 1999.
(60) Provisional application No. 60/111,711, filed on Dec. 8, 1998.

(51) Int. Cl.$^7$ .............................. A61B 1/00; A61B 5/00
(52) U.S. Cl. ...................... 600/407; 600/102; 700/245
(58) Field of Search ............................... 600/407, 103, 600/109, 102; 901/2, 4, 36; 700/65, 83, 85, 264; 348/65

(56) References Cited

U.S. PATENT DOCUMENTS

| | | |
|---|---|---|
| 4,672,963 A | 6/1987 | Barken |
| 4,722,056 A | 1/1988 | Roberts et al. |
| 4,791,934 A | 12/1988 | Brunnett |
| 4,837,703 A | 6/1989 | Kakazu et al. |
| 4,858,149 A | 8/1989 | Quarendon |
| 4,984,157 A | 1/1991 | Cline et al. |
| 5,079,699 A | 1/1992 | Tuy et al. |
| 5,086,401 A | 2/1992 | Glassman et al. |
| 5,098,426 A | 3/1992 | Sklar et al. |
| 5,099,846 A | 3/1992 | Hardy |
| 5,142,930 A | 9/1992 | Allen et al. |
| 5,170,347 A | 12/1992 | Tuy et al. |
| 5,182,641 A | 1/1993 | Diner et al. |
| 5,230,338 A | 7/1993 | Allen et al. |
| 5,230,623 A | 7/1993 | Guthrie et al. |
| 5,235,510 A | 8/1993 | Yamada et al. |
| 5,251,127 A | 10/1993 | Raab |
| 5,257,203 A | 10/1993 | Riley et al. |
| 5,261,404 A | 11/1993 | Mick et al. |
| 5,368,428 A | 11/1994 | Hussey et al. |
| 5,402,801 A | 4/1995 | Taylor |
| 5,417,210 A | 5/1995 | Funda et al. |
| 5,445,166 A | 8/1995 | Taylor |
| 5,531,742 A | 7/1996 | Barken |

(List continued on next page.)

OTHER PUBLICATIONS

Adams et al., "Computer–assisted surgery" IEEE Computer Graphics and Applications (May 1990) pp. 43–51.

(List continued on next page.)

Primary Examiner—Shawna J. Shaw
(74) Attorney, Agent, or Firm—Townsend and Townsend and Crew LLP

(57) ABSTRACT

Systems and methods for performing robotically-assisted surgical procedures on a patient enable an image display device to provide an operator with auxiliary information related to the surgical procedure, in addition to providing an image of the surgical site itself. The systems and methods allow an operator to selectively access and reference auxiliary information on the image display device during the performance of a surgical procedure.

53 Claims, 15 Drawing Sheets

U.S. PATENT DOCUMENTS

| | | | |
|---|---|---|---|
| 5,631,973 A | | 5/1997 | Green |
| 5,695,500 A | | 12/1997 | Taylor et al. |
| 5,762,458 A | | 6/1998 | Wang et al. |
| 5,808,665 A | | 9/1998 | Green |
| 5,855,553 A | * | 1/1999 | Tajima et al. ............... 600/407 |
| 5,876,325 A | | 3/1999 | Mizuno et al. |
| 5,911,036 A | | 6/1999 | Wright et al. |
| 5,931,832 A | | 8/1999 | Jensen |
| 6,292,712 B1 | * | 9/2001 | Bullen ........................ 700/245 |

OTHER PUBLICATIONS

Askew et al., "Ground control testbed for space station freedom robot manipulators" IEEE Virtual Reality Annual International Symposium (Sep. 18–22, 1993), Seattle, Washington, pp. 69–75.

Bjura et al., "Merging virtual objects with the real world: Seeing ultrasound imagery within the patient" Computer Graphics 91992) 26(2):203–210.

Cao et al., "Task and motion analysis in endoscopic surgery" Submitted for Fifth Annual Symposium on Haptic Interfaces for Virtual; Environment and Teloperator Systems for the Winter Meeting of ASME, (1996) pp. 1–32.

Christensen et al., "Model based, sensor directed remediation of underground storage tanks" Proceedings of the IEEE International Conference on Robotics and Automation (1991) pp. 1377–1383.

Dolan et al., "A robot in an operating room: A bull in a china shop?" IEEE/Ninth Annual Conference of the Engineering in Medicine and Biology Society (1987) 2 pages total.

Elder et al., "Specifying user interfaces for safety–critical medical systems" Second Annual International Symposium on Medical Robotics and Computer Assisted Surgery (1995) pp. 148–155.

Gayed et al., "An advanced control micromanipulator for surgical applications" Systems Science (1987) 13:123–133.

Harris et al., "A robotic procedure for transurethral resection of the prostate" Second Annual International Symposium on Medical Robotics and Computer Assisted Surgery (1995) pp. 264–271.

Hunter et al., "A teleoperated microsurgical robot and associated virtual environment for eye surgery" Presence Teleoperators and Virtual Environments, MIT Press (1993) 2(4):264–280.

Hunter et al., "Ophthalmic microsurgical robot and associated virtual environment" Comput. Biol. Med. (1995) 25(2):173–183.

Hurteau et al., "Laparoscopic surgery assisted by a robotic cameraman: Concept and Experimental results" IEEE International Conference on Robotics and Automation (1994) pp. 2286–2289.

Jackson et al., "Force feedback and medical simulation" Interactive Technology and the New Paradigm (1995) pp. 147–151.

Kazerooni, "Design and analysis of the statically balanced direct–drive robot manipulator" Robotics and Computer–Integrated Manufacturing (1989) 6(4):287–293.

Kilmer et al., "Watchdog safety computer design and implementation" RI/SME Robots 8 Conference, (Jun. 1984) pp. 101–117.

Kosugi et al. "An articulated neurosurgical navigation system using MRI and CT Images" IEEE Transactions on Biomedical Engineering (1988) 35(2):147–152.

Ng et al., "Robotic surgery" IEEE Engineering in Medicine and Biology (1993) 120–125.

Paul et al., "Development of a surgical robot for cementless total hip arthroplasty" Clinical Orthopaedics and Related Research (1992) No. 285, pp. 57–66.

Rosenberg, "Human interface hardware for virtual laparoscopic surgery" Interactive Technology and the New Paradigm for Healthcare (1995) Morgan et al., Eds., pp. 322–325.

Schenker et al., :Development of a telemanipulator for dexterity enhanced microsurgery Second Annual International Symposium on Medical Robotics and Computer Assisted Surgery (1995) pp. 81–88.

Taylor et al., Research report: A telerobotic assistant for laparoscopic surgery Computer Science (1994) pp. 1–21.

Taylor et al., "A telerobotic assistant for laparoscopic surgery" IEEE Engineering in Medicine and Biology (1995) pp. 279–288.

Toon, "Eye surgery simulator could help physicians learn and practice new techniques" Research Horizons (Fall 1993) pp. 22–23.

Trivedi et al., "Developing telerobotic systems using virtual reality concepts" Proceedings of the 1993 IEEE/RSJ International Conference on Intelligent Robots and systems(1993) 8 pages total.

Preising et al., "A Literature Review: Robots in Medicine" *IEEE Engineering in Medicine and Biology* (Jun. 1991) pp. 13–22.

* cited by examiner

DEVICES AND METHODS FOR PRESENTING AND REGULATING AUXILIARY INFORMATION ON AN IMAGE DISPLAY OF A TELESURGICAL SYSTEM TO ASSIST AN OPERATOR IN PERFORMING A SURGICAL PROCEDURE

RELATED APPLICATIONS

This application is a continuation-in-part of co-pending U.S. patent applicaton Ser. No. 09/457,406, intitled "Image Shifting Appparatus and Method for a Telerobotic System ," Dec. 7, 1999, and claims the benefit of priority from U.S. (provisionsal) patent application Ser. No. 60/111,711, dentitled "Image Shifting For A Telerobotic System," filed Dec. 8, 1998, the full discolsures of which are incorporated herein by reference. This application is also related to the following patents and patent applications, the full discolsutes of which are incorporated herein by reference: PCT International Application Ser. No. PCT/US98/19508, entitled "Robotic Apparatus," filed on Sep. 18,1998; U.S. patent application Ser. No. 09/418,726, entitled "Surgical Robotic Tools, Data Architecture, and Use," filed on Oct. 15, 1999; U.S. patent application Ser. No. 09/378,173, entailed "Stereo Imaging System for Use in Telerobotic Systems," filed on Aug. 20, 1999; U.S. patent application Ser. No. 09/398,507, entitled "Master Having Redundant Degrees of Freedom," filed Sep. 17, 1999; U.S. patent application Ser. No. 09/288,068, entitled "Aspects of a Control System of a Minimally Invasive Surgical Apparatus," filed Apr. 7, 1999; U.S. patent applicaton Ser. No. 09/373,678, entitled "Camera Reference Control in a Minimally Invasive Surgical Apparatus," filed Aug. 13, 1999; U.S. patent applicaton Ser. No. 09/398,960, entitled "Repositioning and orientation of Master/Slave Relationship in Minimally Invasive Telesurgery," filed Sep. 17, 1999; and U.S. Pat. No. 5,808,665, entitled "Endoscopic Surgical Instrument and Method for Use," issued on Sep. 15, 1998.

BACKGROUND OF THE INVENTION

The present invention is generally related to improved robotic devices, systems and methods, for use in telerobotic surgery.

Minimally invasive medical techniques are aimed at reducing the amount of extraneous tissue which may be damaged during diagnostic or surgical procedures, thereby reducing patient recovery time, discomfort, and deleterious side effects. Many surgeries are performed each year in the United States. A significant amount of these surgeries can potentially be performed in a minimally invasive manner. However, only a relatively small percentage of surgeries currently use minimally invasive techniques due to limitations of minimally invasive surgical instruments and techniques currently used and the difficulty experienced in performing surgeries using such traditional instruments and techniques.

Advances in minimally invasive surgical technology could dramatically increase the number of surgeries performed in a minimally invasive manner. The average length of a hospital stay for a standard surgery is significantly longer than the average length for the equivalent surgery performed in a minimally invasive surgical manner. Thus, expansion in the use of minimally invasive techniques could save millions of hospital days, and consequently millions of dollars annually, in hospital residency costs alone. Patient recovery times, patient discomfort, surgical side effects, and time away from work can also be reduced by expanding the use of minimally invasive surgery.

Traditional forms of minimally invasive surgery include endoscopy. One of the more common forms of endoscopy is laparoscopy, which is minimally invasive inspection or surgery within the abdominal cavity. In traditional laparoscopic surgery a patient's abdominal cavity is insufflated with gas and cannula sleeves are passed through small (approximately ½ inch) incisions in the musculature of the patient's abdomen to provide entry ports through which laparoscopic surgical instruments can be passed in a sealed fashion.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by an approximately 12-inch long extension tube, for example, so as to permit the surgeon to introduce the end effector to the surgical site and to control movement of the end effector relative to the surgical site from outside a patient's body.

To perform surgical procedures, the surgeon typically passes these working tools or instruments through the cannula sleeves to the internal surgical site and manipulates the instruments or tools from outside the abdomen by sliding them in and out through the cannula sleeves, rotating them in the cannula sleeves, levering (i.e., pivoting) the instruments against the abdominal wall and actuating the end effectors on the distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site via the laparoscopic camera. Typically, the laparoscopic camera is also introduced through the abdominal wall so as to capture an image of the surgical site. Similar endoscopic techniques are employed in, e.g., arthroscopy, retroperitoneoscopy, pelviscopy, nephroscopy, cystoscopy, cistemoscopy, sinoscopy, hysteroscopy, urethroscopy, and the like.

There are many disadvantages relating to such traditional minimally invasive surgical (MIS) techniques. For example, existing MIS instruments deny the surgeon the flexibility of tool placement found in open surgery. Difficulty is experienced in approaching the surgical site with the instruments through the small incisions. The length and construction of many endoscopic instruments reduces the surgeon's ability to feel forces exerted by tissues and organs on the end effector of the associated instrument. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment to the expansion of the use of minimally invasive surgery.

Minimally invasive telesurgical systems for use in surgery have been and are still being developed to increase a surgeon's dexterity as well as to permit a surgeon to operate on a patient in an intuitive manner. Telesurgery is a general term for surgical systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement during the surgical procedure on the visual display. While viewing typically a three-dimensional image of the surgical site on the visual display, the surgeon performs the surgical procedures on the patient by manipulating master control devices at the remote location, which master control devices control motion of the remotely controlled instruments.

Typically, such a telesurgery system can be provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like.

One object of the present invention is to provide improved telesurgery systems, devices and methods for use in surgery. Another object of the invention is to provide a telesurgical system and method whereby auxiliary information related to a surgical procedure to be performed by the telesurgical system can be selectively displayed on a viewer of the system, together with an image of the surgical site captured by an image capture device, such as an endoscope, of the system, so as to enable an operator of the system selectively to reference such auxiliary information on the viewer during the performance of the surgical procedure. In this manner the surgical procedure can typically be performed with greater confidence, safety, efficacy and in some cases greater accuracy.

SUMMARY OF THE INVENTION

According to one aspect of the invention, there is provided a method of performing a surgical procedure on a patient. The method typically comprises positioning a surgical work station of a robotically controlled surgical system and a patient on which a surgical procedure is to be performed in close proximity relative to each other, directing a field of view of an image capture device of the surgical work station at a surgical site on the patient, at which site the surgical procedure is to be performed, and introducing at least one robotically controlled surgical instrument on the surgical work station to the surgical site so that an end effector of the surgical instrument is within the field of view of the image capture device.

The method typically further comprises displaying an image of the surgical site and the end effector on a display area of an image display at an operator control station of the surgical system. The image display is typically operatively connected to the image capture device so as to display, on the display area, the image of the surgical site and the end effector captured by the image capture device. The method can further include permitting an operator of the surgical system to manipulate a master control at the operator control station whilst viewing the image of the surgical site on the image display, the master control being operatively associated with the surgical instrument thereby to cause the end effector to move in response to manipulation of the master control so as to perform at least part of the surgical procedure on the patient at the surgical site.

The method yet further typically comprises operatively linking the image display to a source of selectively accessible auxiliary information related to the surgical procedure to be performed, enabling the operator selectively to access the source of auxiliary information from the operator control station so as to forward the auxiliary information to the image display, causing the auxiliary information to be displayed across the display area of the image display in response to the operator selectively accessing the source of auxiliary information at the operator control station and enabling the operator selectively to move the auxiliary information when displayed on the image display relative to the image of the surgical site displayed on the image display.

The master control is typically operatively linked with the source of auxiliary information, enabling the operator selectively to access the source of auxiliary information then including permitting the operator selectively to disassociate the master control from the surgical instrument and to use the master control to access the source of Lauxiliary information so as to enable the auxiliary information to be displayed on the display area of the image display.

According to another aspect of the invention, there is provided a method of performing a surgical procedure on a patient, the method comprising manipulating a master control whilst viewing a real time image of a surgical site on an image display, moving an end effector in response to manipulation of the master control so as to perform at least part of a surgical procedure at the surgical site and selectively accessing a source of auxiliary information by means of the master control. The method typically further comprises displaying the auxiliary information on the image display.

BRIEF DESCRIPTION OF THE DRAWINGS

The invention will now be described, by way of example only, and with reference to the accompanying diagrammatic drawings, in which.

DESCRIPTION OF THE PREFERRED EMBODIMENTS

Figure 1:
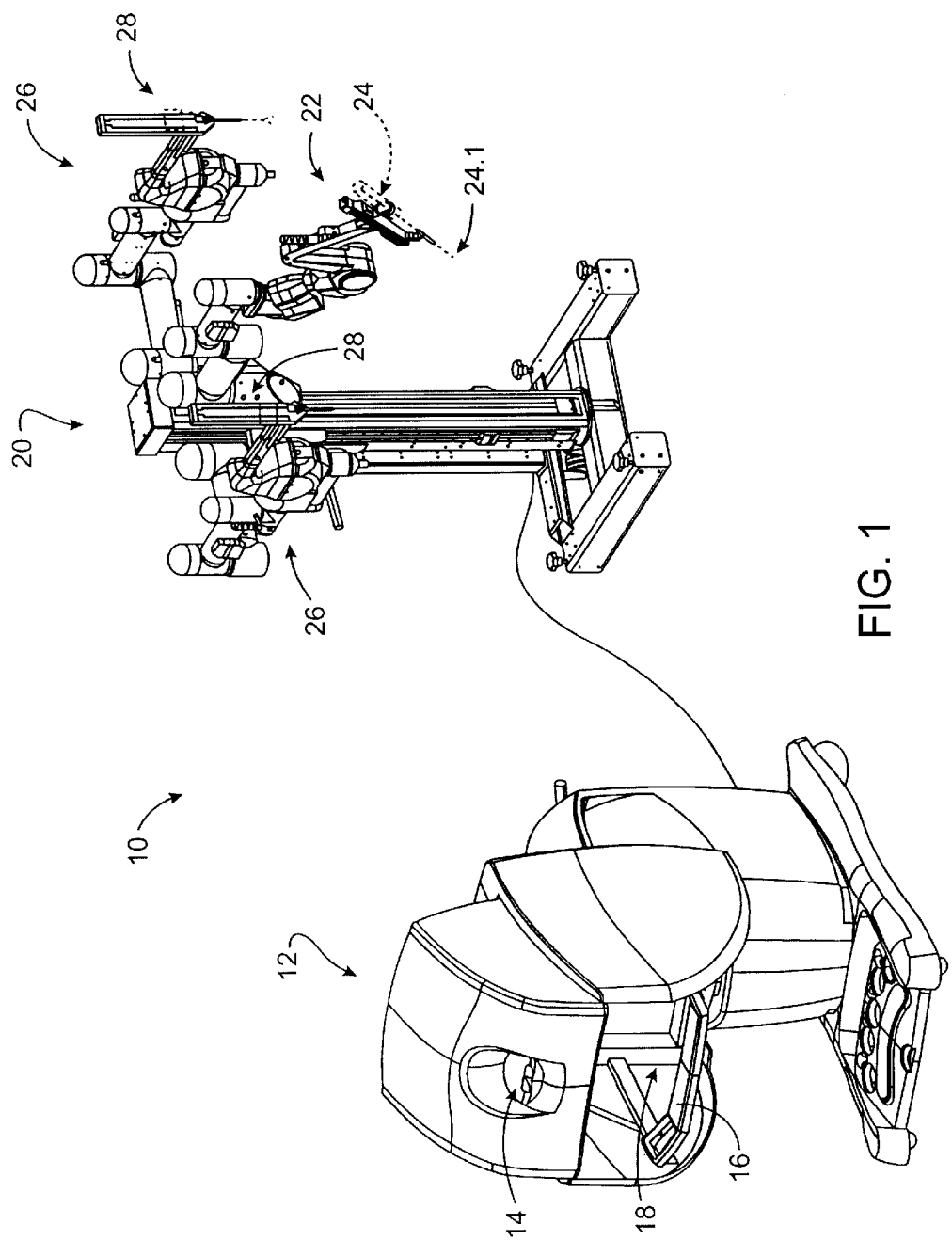
FIG. 1 shows a three-dimensional view of an operator control station, or surgeon's console, and a surgical work station, or cart, of a telesurgical system in accordance with the invention, the cart carrying three robotically controlled arms, the movement of the arms being remotely controllable from the control station.
Figure 6:
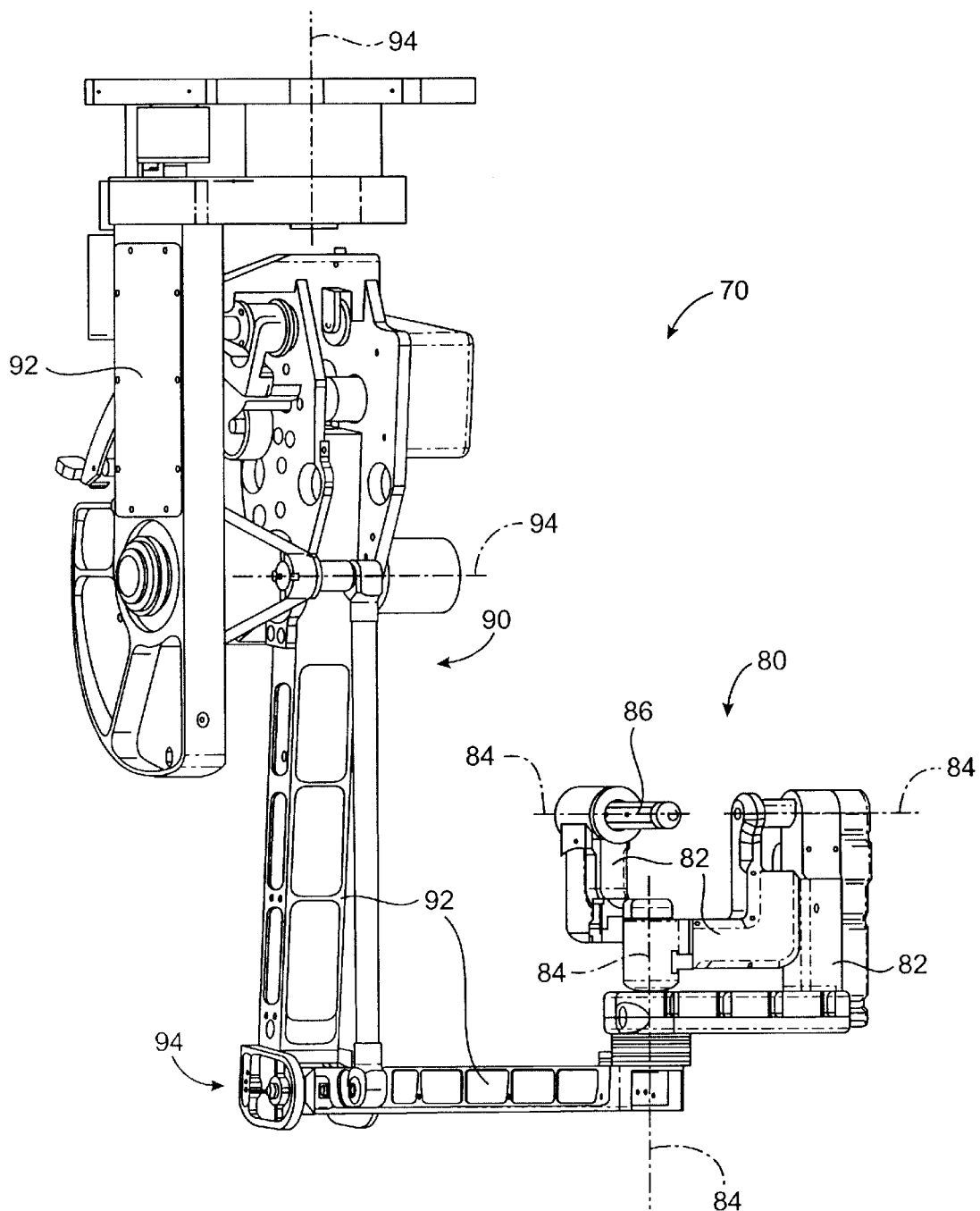
FIG. 6 shows a three-dimensional view of one of the master control devices of the control station shown in FIG. 1, the master control device including a hand-held part, or wrist gimbal, and an articulated arm portion on which the hand-held part is mounted.

Referring to FIG. 1 of the drawings, a minimally invasive telesurgical system, or robotically controlled surgical system, in accordance with the invention is generally indicated by reference numeral 10. The system 10 includes a control station, or surgeon's console, generally indicated by reference numeral 12. The station 12 includes an image display or viewer 14 where an image of a surgical site is displayed in use. A support 16 is provided on which an operator, typically a surgeon, can rest his or her forearms while gripping two master control devices, one of which is shown in FIG. 6 of the drawings, one in each hand. The master controls are positioned in a space 18 inwardly beyond the support 16. When using the control station 12, the surgeon typically sits in a chair in front of the control station 12, positions his or her eyes in front of the viewer 14 and grips the master controls one in each hand while resting his or her forearms on the support 16.

The system 10 further includes a surgical work station, or cart, generally indicated by reference numeral 20. In use, the cart 20 is positioned in close proximity to a patient requiring surgery and is then normally caused to remain stationary until a surgical procedure to be performed by means of the system 10 has been completed. The cart 20 typically has wheels or castors to render it mobile. The station 12 is typically positioned remote from the cart 20 and can be separated from the cart 20 by a great distance, even miles away, but will typically be used within an operating room with the cart 20.

The cart 20 typically carries at least three robotic arm assemblies. One of the robotic arm assemblies, indicated by reference numeral 22, is arranged to hold an image capture device 24, e.g., an endoscope, or the like. Each of the other two arm assemblies 26, 26 respectively, is arranged to hold a robotically controlled surgical instrument 28. The endoscope 24 has an object viewing end 24.1 at a remote end of an elongate shaft thereof. It will be appreciated that the endoscope 24 has an elongate shaft to permit its viewing end 24.1 to be inserted through an entry port in a patient's body so as to access an internal surgical site. The endoscope 24 is operatively connected to the viewer 14 to display an image captured at its viewing end 24.1 on a display area of the viewer 14. Each robotic arm assembly 26, 26 is normally operatively connected to one of the master controls. Thus, the movement of the robotic arm assemblies 26, 26 is controlled by manipulation of the master controls. The instruments 28 on the robotic arm assemblies 26, 26 have end effectors which are mounted on wrist members which are pivotally mounted on distal ends of elongate shafts of the instruments 28. It will be appreciated that the instruments 28 have elongate shafts to permit the end effectors to be inserted through entry ports in a patient's body so as to access the internal surgical site. Movement of the end effectors relative to the ends of the shafts of the instruments 28 is also controlled by the master controls. When a surgical procedure is to be performed, the cart 20 carrying the robotic arms 22, 26, 26 is wheeled to the patient and is normally maintained in a stationary position relative to, and in close proximity to, the patient, during the surgical procedure.

Figure 2:
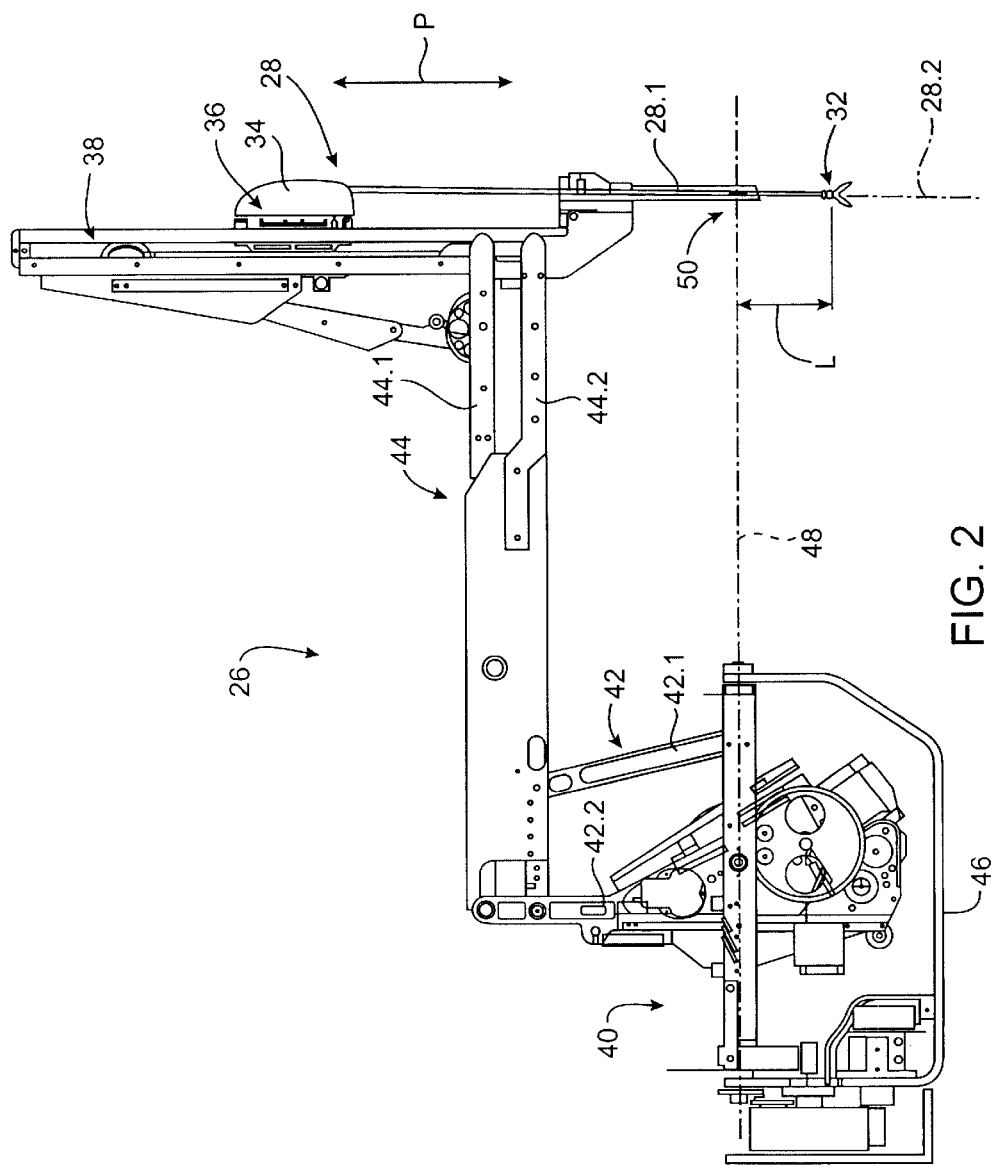
FIG. 2 shows, at an enlarged scale, a side view of a robotic arm and surgical instrument assembly of the surgical station shown in FIG. 1.
Figure 3:
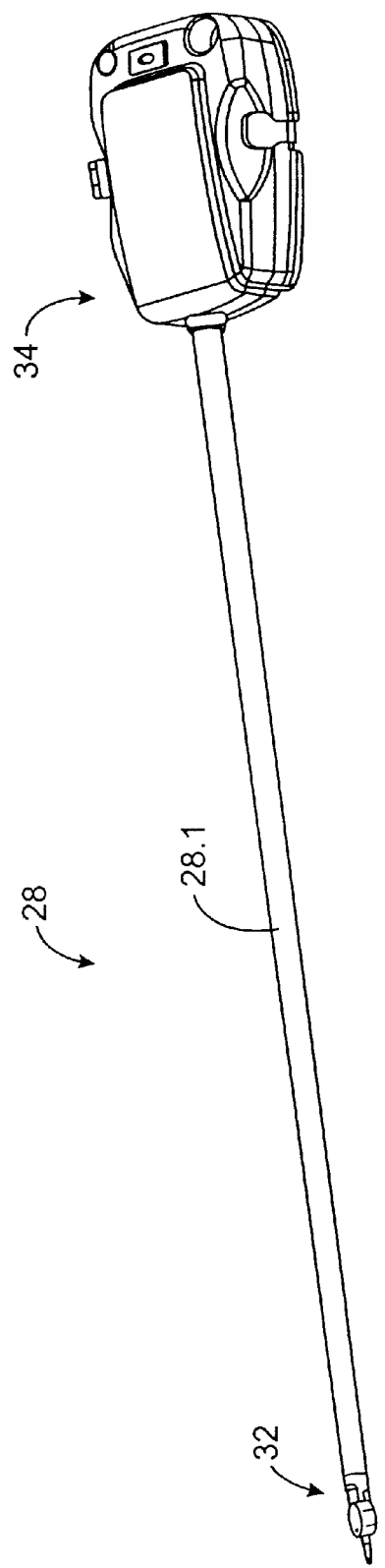
FIG. 3 shows, at an enlarged scale, a three-dimensional view of a typical surgical instrument of the system shown in FIG. 1.

In FIG. 2 of the drawings, one of the robotic arm assemblies 26 is shown in greater detail, and on an enlarged scale. Each assembly 26 typically has a surgical instrument, schematically and generally indicated by reference numeral 28, releasably mounted thereon. FIG. 3 indicates the general appearance of a typical surgical instrument 28 in greater detail.

Referring now to FIG. 3 of the drawings, the surgical instrument 28 includes an elongate shaft 28.1. The wrist-like mechanism, generally indicated by reference numeral 32, is located at a working end of the shaft 28.1. A housing 34, arranged releasably to couple the instrument 28 to the robotic arm 26, is located at an opposed end of the shaft 28.1. In FIG. 2, and when the instrument 28 is coupled or mounted on the robotic arm 26, the shaft 28.1 extends along an axis indicated at 28.2. The instrument 28 is typically releasably mounted on a carriage 36, which can be driven to translate along a linear guide formation 38 of the arm 26 in the direction of arrows P.

The robotic arm 26 includes a cradle, generally indicated at 40, an upper arm portion 42, a forearm portion 44 and the guide formation 38. The cradle 40 is pivotally mounted on a plate 46 in a gimbaled fashion to permit rocking movement of the cradle 40 about a pivot axis 48. The upper arm portion 42 includes link members 42.1, 42.2 and the forearm portion 44 includes link members 44.1, 44.2. The link members 42.1, 42.2 are pivotally mounted on the cradle 40 and are pivotally connected to the link members 44.1, 44.2. The link members 44.1, 44.2 are pivotally connected to the guide formation 38. The pivotal connections between the link members 42.1, 42.2, 44.1, 44.2, the cradle 40, and the guide formation 38 are arranged to constrain the robotic arm 26 to move in a specific manner. The movement of the robotic arm 26 is illustrated schematically in FIG. 4.

Figure 4:
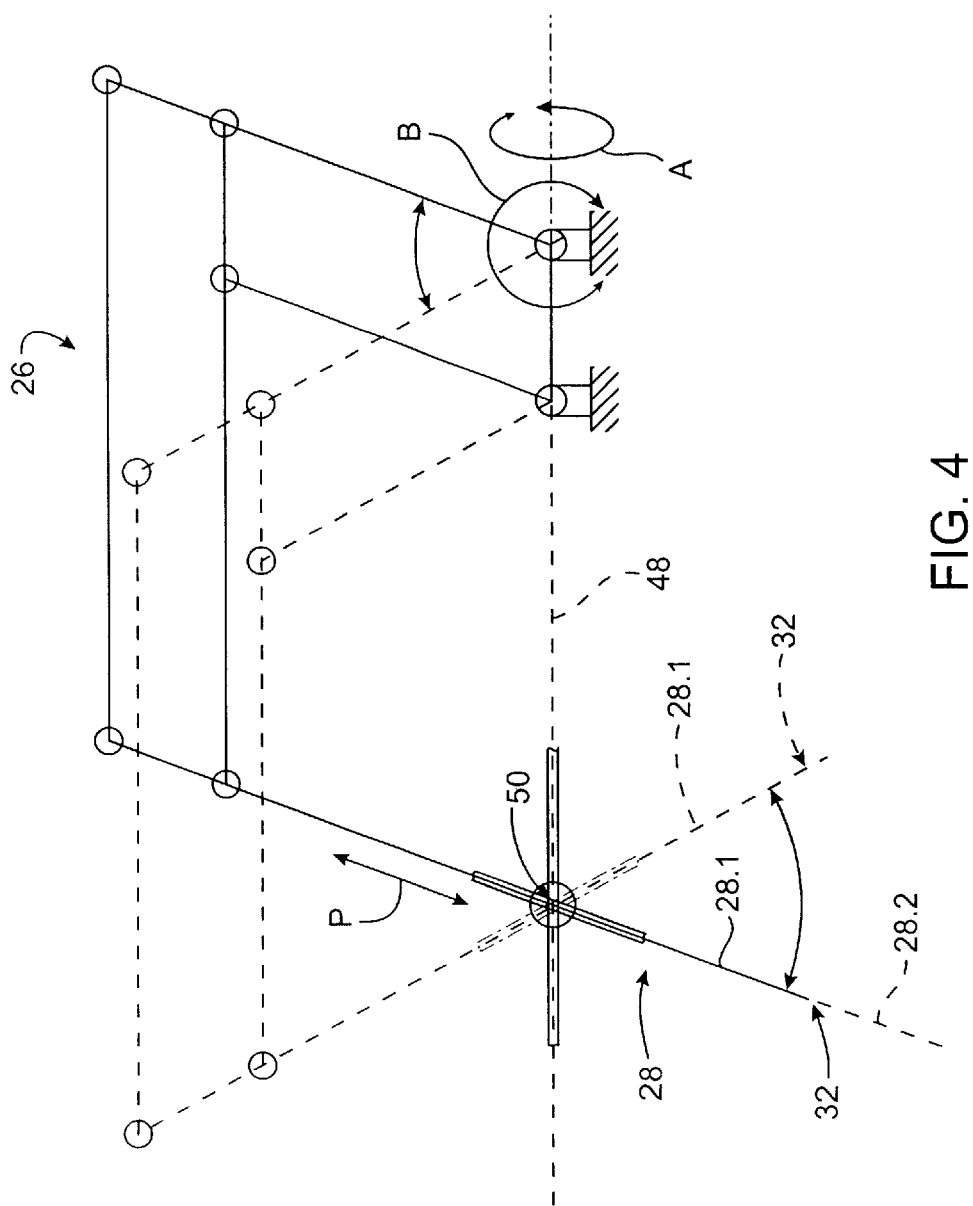
FIG. 4 shows a schematic kinematic diagram corresponding to the side view of the robotic arm shown in FIG. 2, and indicates the arm having been displaced from one position into another position.

With reference to FIG. 4 of the drawings, the solid lines schematically indicate one position of the robotic arm 26 and the dashed lines indicate another possible position into which the arm 26 can be displaced from the position indicated in solid lines.

It will be understood that the axis 28.2 along which the shaft 28.1 of the instrument 28 extends when mounted on the robotic arm 26 pivots about a pivot center or fulcrum 50. Thus, irrespective of the movement of the robotic arm 26, the pivot center 50 normally remains in the same position relative to the stationary cart 20 on which the arm 26 is mounted. In use, the pivot center 50 is positioned at a port of entry into a patient's body when an internal surgical procedure is to be performed. It will be appreciated that the shaft 28.1 extends through such a port of entry, the wrist-like mechanism 32 then being positioned inside the patient's body. Thus, the general position of the mechanism 32 relative to the surgical site in a patient's body can be changed by movement of the arm 26. Since the pivot center 50 is coincident with the port of entry, such movement of the arm does not excessively effect the surrounding tissue at the port of entry.

As can best be seen with reference to FIG. 4, the robotic arm 26 provides three degrees of freedom of movement to the surgical instrument 28 when mounted thereon. These degrees of freedom of movement are firstly the gimbaled motion indicated by arrows A, pivoting or pitching movement as indicated by arrows B and the linear displacement in the direction of arrows P. Movement of the arm 26 as indicated by arrows A, B and P is controlled by appropriately positioned actuators, e.g., electrical motors, or the like, which respond to inputs from an associated master control to drive the arm 26 to a required position as dictated by movement of the master control. Appropriately positioned sensors, e.g., potentiometers, encoders, or the like, are provided on the arm 26 to enable a control system of the minimally invasive telesurgical system 10 to determine joint positions, as described in greater detail herein below. It will be appreciated that whenever "sensors" are referred to in this specification, the term is to be interpreted widely to include any appropriate sensors, such as, for example, positional sensors, velocity sensors, or the like. It will be appreciated that by causing the robotic arm 26 selectively to displace from one position to another, the general position of the wrist-like mechanism 32 relative to the surgical site can be varied during the performance of a surgical procedure.

Figure 5:
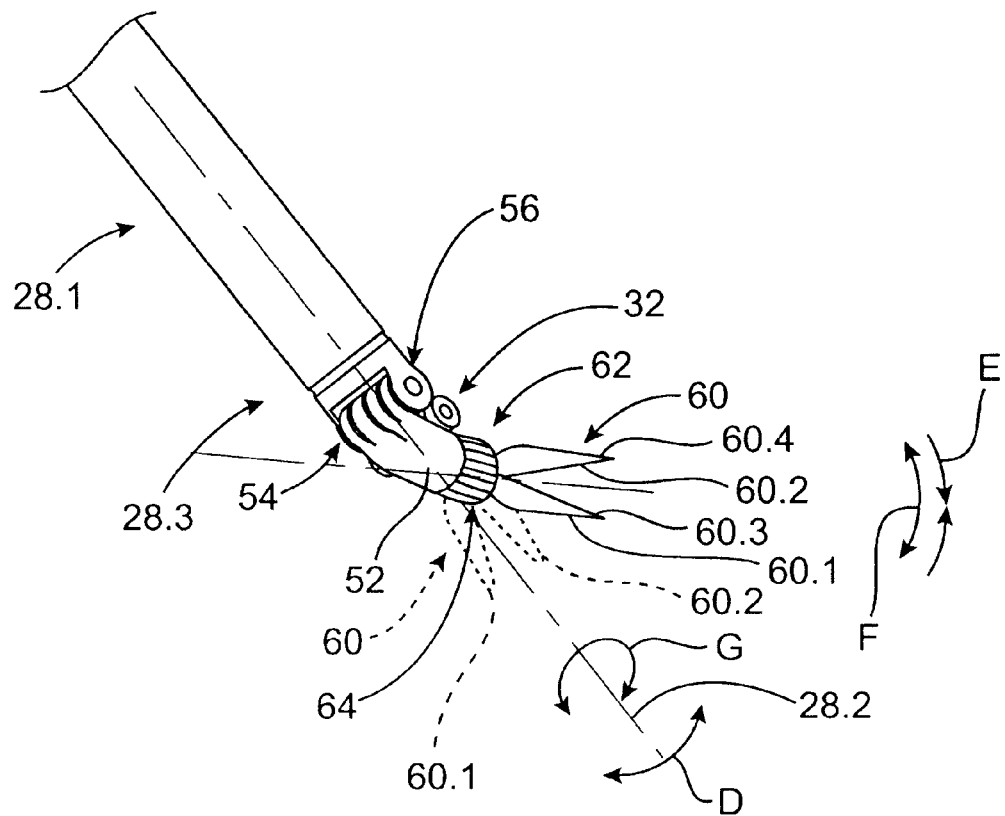
FIG. 5 shows, at an enlarged scale, a wrist member and an end effector of the surgical instrument shown in FIG. 3, the wrist member and the end effector being movably mounted on a working end of a shaft of the surgical instrument.

Referring now to FIG. 5 of the drawings, the wrist-like mechanism 32 will now be described in greater detail. In FIG. 5, the working end of the shaft 28.1 is indicated at 28.3. The wrist-like mechanism 32 includes a wrist member 52. One end portion of the wrist member 52 is pivotally mounted in a clevis, generally indicated at 54, on the end 28.3 of the shaft 28.1 by means of a pivotal connection 56. The wrist member 52 can pivot in the direction of arrows D about the pivotal connection 56. An end effector, generally indicated by reference numeral 60, is pivotally mounted on an opposed end of the wrist member 52. The end effector 60 is in the form of, e.g., a clip applier for anchoring clips during a surgical procedure, or the like. Accordingly, the end effector 60 has two parts 60.1, 60.2 together defining a jaw-like arrangement.

It will be appreciated that the end effector 60 can be in the form of any desired surgical tool, e.g., having two members, or fingers, which pivot relative to each other, such as, for example, scissors, pliers for use as needle drivers, or the like. Instead, it can include a single working member, e.g., a scalpel, cautery electrode, or the like. When a tool other than a clip applier is required during the surgical procedure, the tool 28 is simply removed from its associated arm 26 and replaced with an instrument bearing the required end effector, e.g., a scissors, or pliers, or the like.

The end effector 60 is pivotally mounted in a clevis, generally indicated by reference numeral 62, on an opposed end of the wrist member 52, by means of a pivotal connection 64. It will be appreciated that free ends 60.3, 60.4 of the parts 60.1, 60.2 are angularly displaceable about the pivotal connection 64 toward and away from each other as indicated by arrows E, F. It will further be appreciated that the members 60.1, 60.2 can be displaced angularly about the pivotal connection 64 to change the orientation of the end effector 60 as a whole, relative to the wrist member 52. Thus, each part 60.1, 60.2 is angularly displaceable about the pivotal connection 64 independently of the other, so that the end effector 60, as a whole, is angularly displaceable about the pivotal connection 64 as indicated in dashed lines in FIG. 5. Furthermore, the shaft 28.1 is rotatably mounted on the housing 34 for rotation as indicated by the arrows G. Thus, the end effector 60 has three degrees of freedom of movement relative to the arm 26, namely, rotation about the axis 28.2 as indicated by arrows G, angular displacement as a whole about the pivot 64 and angular displacement about the pivot 56 as indicated by arrows D. By moving the end effector 60 within its three degrees of freedom of movement, its orientation relative to the end 28.3 of the shaft 28.1 can selectively be varied. It will be appreciated that movement of the end effector 60 relative to the end 28.3 of the shaft 28.1 is controlled by appropriately positioned actuators, e.g., electrical motors, or the like, which respond to inputs from the associated master control to drive the end effector 60 to a required orientation as dictated by movement of the master control. Furthermore, appropriately positioned sensors, e.g., encoders, or potentiometers, or the like, are provided to permit the control system of the minimally invasive telesurgical system 10 to determine joint positions as described in greater detail herein below.

One of the master controls is indicated generally in FIG. 6 by reference numeral 70. A hand held part, or wrist gimbal, of the master control 70 is generally indicated by reference numeral 80. Part 80 has an articulated arm portion including a plurality of members or links 82 connected together by pivotal connections or joints 84. The surgeon grips the part 80 by positioning his or her thumb and index finger over a pincher formation 86. When the pincher formation 86 is squeezed between the thumb and index finger, the fingers or end effector elements 60.1, 60.2 of the end effector 60 close.

When the thumb and index finger are moved apart, the fingers 60.1, 60.2 of the end effector 60 move apart in sympathy with the moving apart of the pincher formation 86. The joints 84 of the part 80 are operatively connected to actuators, e.g., electric motors, or the like, to provide for, e.g., force feedback, gravity compensation, and/or the like. Furthermore, appropriately positioned sensors, e.g., encoders, or potentiometers, or the like, are positioned on each joint 84 of the part 80, so as to enable joint positions of the part 80 to be determined by a control system of the surgical system 10.

The part 80 is typically mounted on an articulated arm 90. The articulated arm 90 includes a plurality of links 92 connected together at pivotal connections or joints 94. It will be appreciated that also the articulated arm 90 has appropriately positioned actuators, e.g., electric motors, or the like, to provide for, e.g., force feedback, gravity compensation, and/or the like. Furthermore, appropriately positioned sensors, e.g., encoders, or potentiometers, or the like, are positioned on the joints 94 so as to enable joint positions of the articulated arm 90 to be determined by the control system as described in greater detail herein below.

To move the orientation of the end effector 60 and/or its position along a translational path, the surgeon simply moves the pincher formation 86 to cause the end effector 60 to move to where he wants the end effector 60 to be with reference to the image viewed at the viewer 14. The end effector position and/or orientation can be arranged to follow that of the pincher formation 86.

The actuators and sensors associated with the robotic arms 26, 26 and the surgical instruments 28, 28 mounted thereon, and the actuators and sensors associated with the master control devices 70, 70 are operatively linked in the control system. The control system typically includes at least one processor, typically a plurality of processors, for effecting control between master control device input and responsive robotic arm and surgical instrument output and for effecting control between robotic arm and surgical instrument input and responsive master control output in the case of, e.g., force feedback, or the like.

Figure 7:
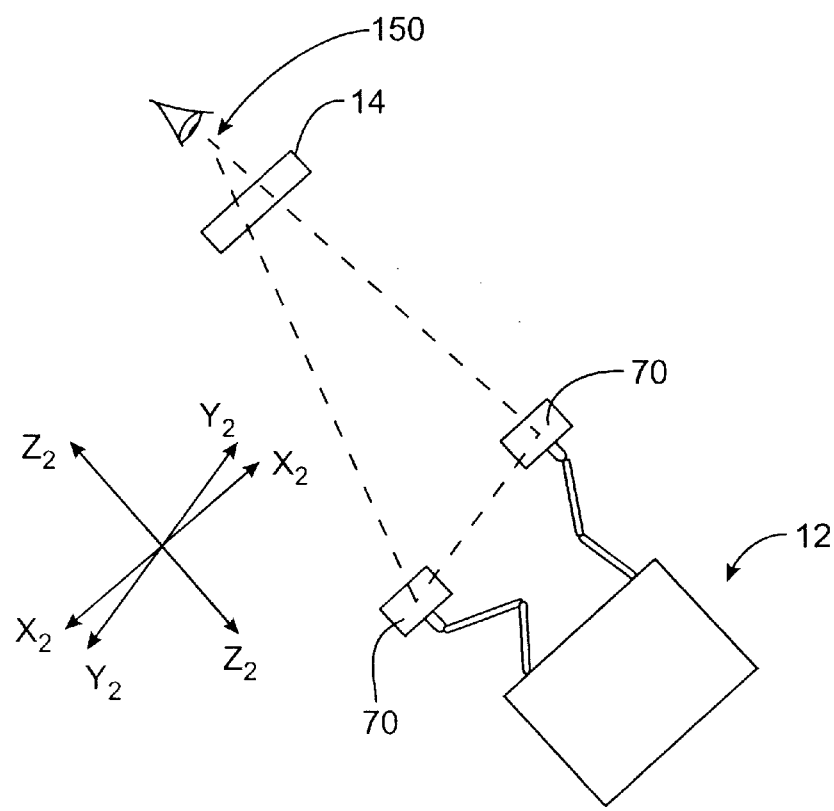
FIG. 7 shows a schematic three-dimensional drawing indicating the positions of the end effectors relative to a viewing end of an endoscope on the surgical station and the corresponding positions of the master control devices relative to the eyes of an operator, typically a surgeon, at the control station.
Figure 7:
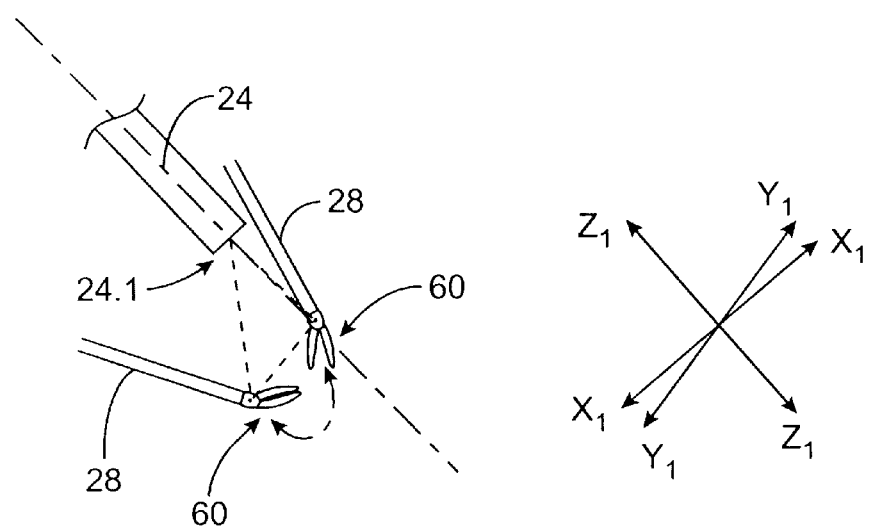

In use, and as schematically indicated in FIG. 7 of the drawings, the surgeon views the surgical site through the viewer 14. The end effector 60 carried on each arm 26 is caused to perform positional and orientational movements in response to movement and action inputs on its associated master control. The master controls are indicated schematically at 70, 70. It will be appreciated that during a surgical procedure images of the end effectors 60 are captured by the endoscope 24 together with the surgical site and are displayed on the viewer 14 so that the surgeon sees the responsive movements and actions of the end effectors 60 as he or she controls such movements and actions by means of the master control devices 70, 70. The control system is typically arranged automatically to cause end effector orientational and positional movement as viewed in the image at the viewer 14 to be mapped onto orientational and positional movement of the pincher formation 86 of its associated master control 70, as will be described in greater detail herein below.

The operation of the control system of the surgical system or apparatus 10 will now be described. In the description which follows, the control system will be described with reference to a single master control 70 and its associated robotic arm 26 and surgical instrument 28. The master control 70 will be referred to simply as "master" and its associated robotic arm 26 and surgical instrument 28 will be referred to simply as "slave."

Figure 8:
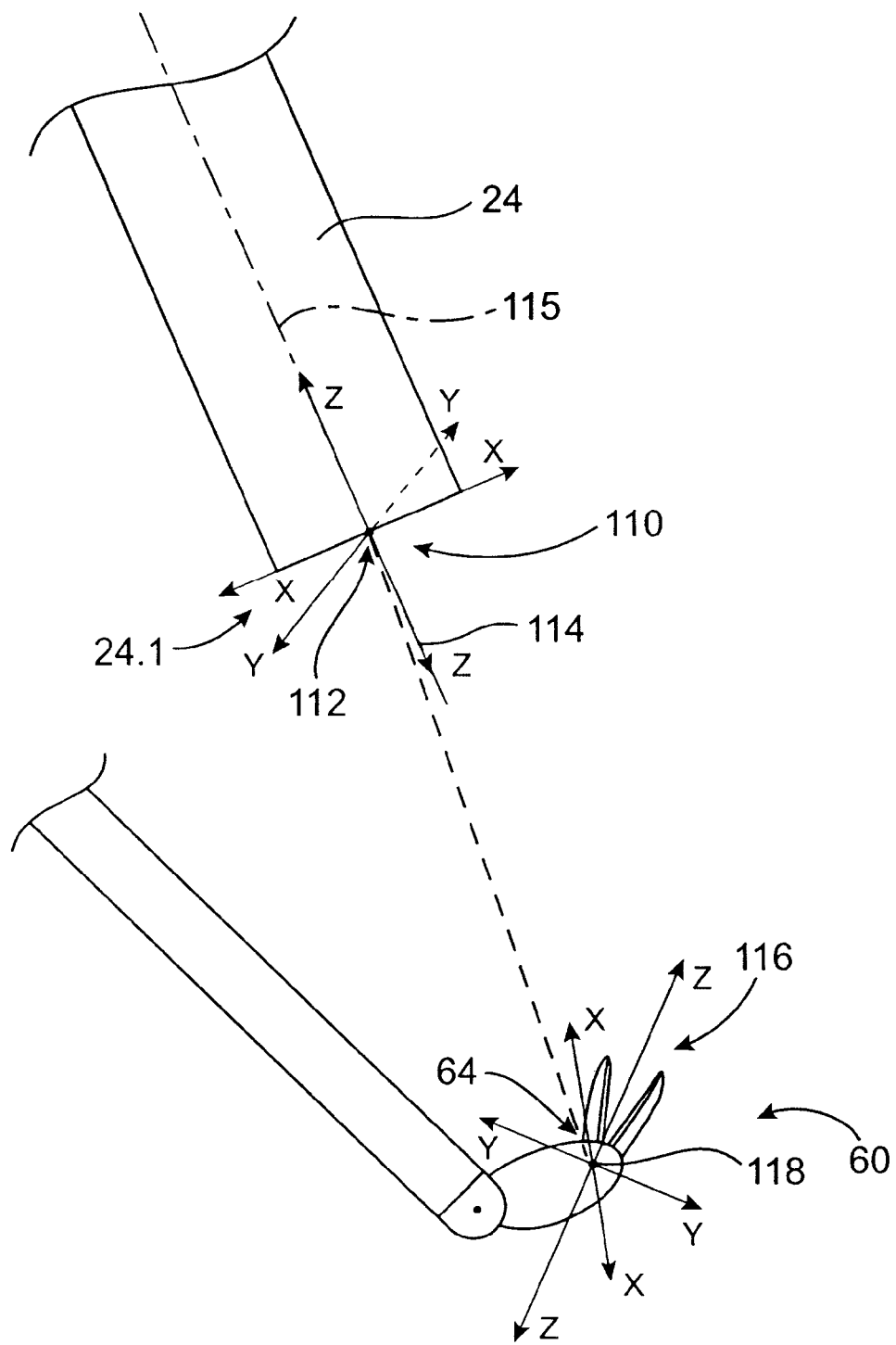
FIG. 8 shows a schematic three-dimensional drawing indicating the position and orientation of an end effector relative to a camera Cartesian coordinate reference system at a viewing end of the endoscope.

The method whereby control between master movement and corresponding slave movement is achieved by the control system of the minimally invasive surgical apparatus will now be described with reference to FIGS. 8 to 10 of the drawings in overview fashion. For a more detailed description of control between master movement and corresponding slave movement refer to Applicant's co-pending U.S. application Ser. No. 09/373,678, entitled "Camera Referenced Control in a Minimally Invasive Surgical Apparatus," filed Aug. 13, 1999, which is fully incorporated herein by reference as if part of this specification.

Control between master and slave movement is achieved by comparing master position and orientation in an eye Cartesian coordinate reference system with slave position and orientation in a camera Cartesian coordinate reference system. For ease of understanding and economy of words, the term "Cartesian coordinate reference system" will simply be referred to as "frame" in the rest of this specification. Accordingly, when the master is stationary, the slave position and orientation in the camera frame is compared with the master position and orientation in the eye frame, and should the position and/or orientation of the slave in the camera frame not correspond with the position and/or orientation of the master in the eye frame, the slave is caused to move to a position and/or orientation in the camera frame at which its position and/or orientation in the camera frame does correspond with the position and/or orientation of the master in the eye frame. In FIG. 8, the camera frame is generally indicated by reference numeral 110 and the eye frame is generally indicated by reference numeral 150 in FIG. 9.

When the master, or pincher formation 86, is moved into a new position and/or orientation in the eye frame 150, the new master position and/or orientation does not correspond with the previously corresponding slave position and/or orientation in the camera frame 110. The control system then causes the slave to move into a new position and/or orientation in the camera frame 110 at which new position and/or orientation, its position and orientation in the camera frame 110 does correspond with the new position and/or orientation of the master in the eye frame 150.

It will be appreciated that the control system includes at least one, and typically a plurality of processors which compute new corresponding positions and orientations of the slave in response to master movement input commands on a continual basis at a rate corresponding to the processing cycle rate of the control system. A typical processing cycle rate of the control system is about 1300 Hz. Thus, when the master is moved from one position to a next position, the corresponding movement of the slave to respond is computed at about 1300 Hz. Naturally, the control system can have any appropriate processing cycle rate depending on the processor or processors used in the control system.

The camera frame 110 is typically positioned such that its origin 112 is at the viewing end 24.1 of the endoscope 24. Conveniently, the z axis of the camera frame 110 extends axially along a viewing axis 114 of the endoscope 24. Although, in FIG. 8, the viewing axis 114 is shown in coaxial alignment with a shaft axis 115 of the endoscope 24, it is to be appreciated that the viewing axis 114 can be angled relative thereto. Thus, the endoscope can be in the form of an angled scope. Naturally, the x and y axes are positioned in a plane perpendicular to the z axis. The endoscope is typically angularly displaceable about its shaft axis. The x, y and z axes are fixed relative to the viewing axis 114 of the endoscope 24 so as to displace angularly about the shaft axis in sympathy with angular displacement of the endoscope 24 about its shaft axis 115.

To enable the control system to determine slave position and orientation, a frame is defined on, or attached to, the end effector 60. This frame is referred to as an end effector frame or slave tip frame, in the rest of this specification, and is generally indicated by reference numeral 116. Conveniently, the end effector frame 116 has its origin at the pivotal connection 64. However, depending on the type of end effector used, the origin may be offset relative to such a pivotal connection should an improved or more intuitive response between master input and slave output be achieved thereby. For the end effector 60 as shown in the drawings, one of the axes, e.g., the z axis, of the frame 116 is defined to extend along an axis of symmetry, or the like, of the end effector 60. Naturally, the x and y axes then extend perpendicularly to the z axis. It will be appreciated that the orientation of the slave is then defined by the orientation of the frame 116 having its origin at the pivotal connection 64, relative to the camera frame 110. Similarly, the position of the slave is then defined by the position of the origin 118 of the frame 116 relative to the camera frame 110.

Figure 9:
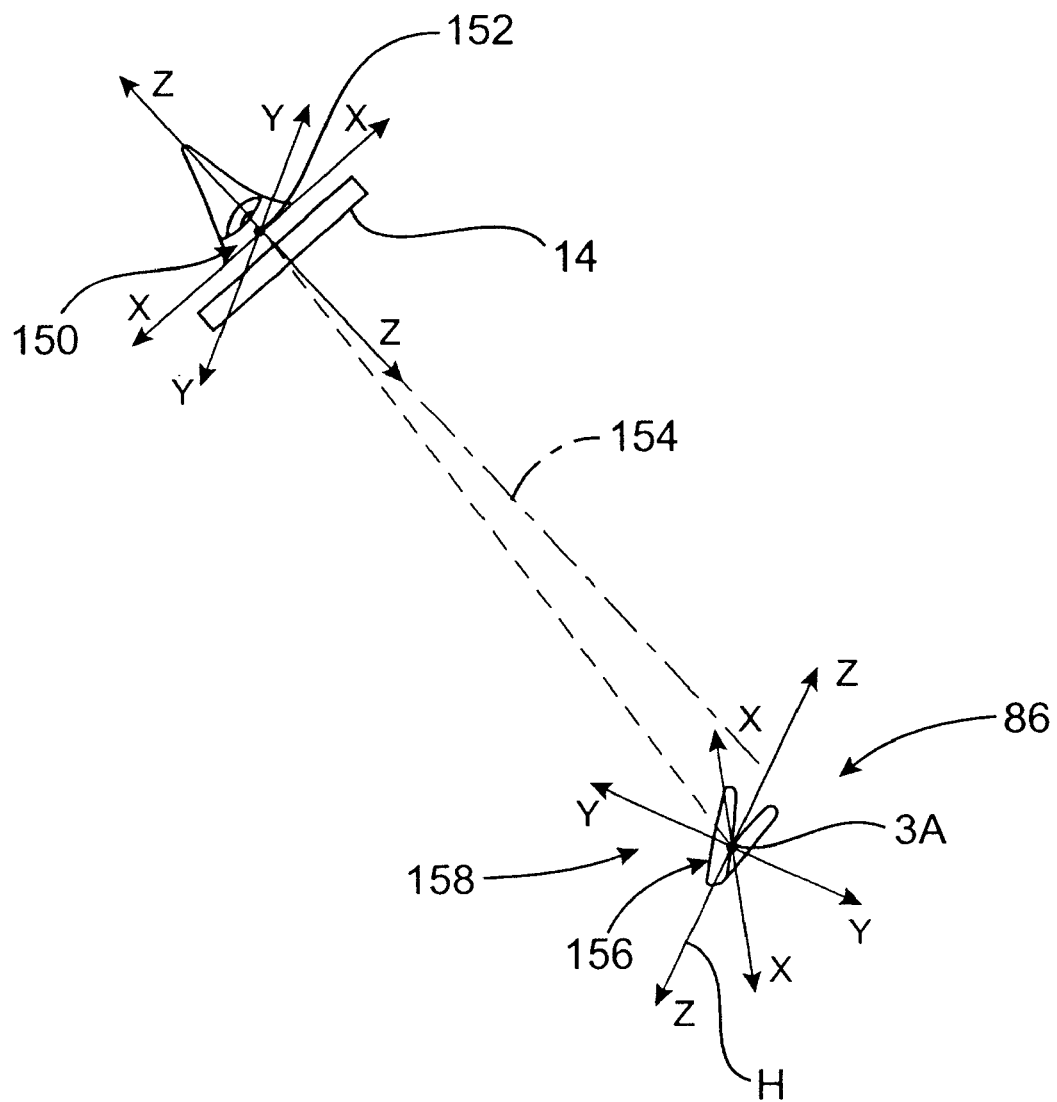
FIG. 9 shows a schematic three-dimensional drawing indicating the position and orientation of a pincher formation of one of the master control devices relative to an eye Cartesian coordinate reference system at a viewer of the control station.

Referring now to FIG. 9 of the drawings, the eye frame 150 is typically chosen such that its origin corresponds with a position 152 where the surgeon's eyes are normally located when he or she is viewing the surgical site at the viewer 14. The z axis typically extends along a line of sight of the surgeon, indicated by axis 154, when viewing the surgical site through the viewer 14. Naturally, the x and y axes extend perpendicularly from the z axis at the origin 152. Conveniently, the y axis is chosen to extend generally vertically relative to the viewer 14 and the x axis is chosen to extend generally horizontally relative to the viewer 14.

To enable the control system to determine master position and orientation in the viewer frame 150, an appropriate point, e.g., point 3A, is chosen on the master to define an origin 156 of a master or master tip frame 158. It will be appreciated that the point relative to the master at which the origin 156 of the master frame 158 is attached is chosen to enhance intuitive response between master and slave and can thus be at any appropriate location relative to the master. Conveniently, the z axis of the master frame 158 on the master extends along an axis of symmetry of the pincher formation 86 which extends coaxially along a rotational axis H of the pincher formation 86 relative to the rest of the master 70. The x and y axes then extend perpendicularly from the rotational axis H at the origin 3A. Accordingly, orientation of the master within the eye frame 150 is defined by the orientation of the master frame 158 relative to the eye frame 150. The position of the master in the eye frame 150 is defined by the position of the origin 156 at 3A relative to the eye frame 150.

Figure 10:
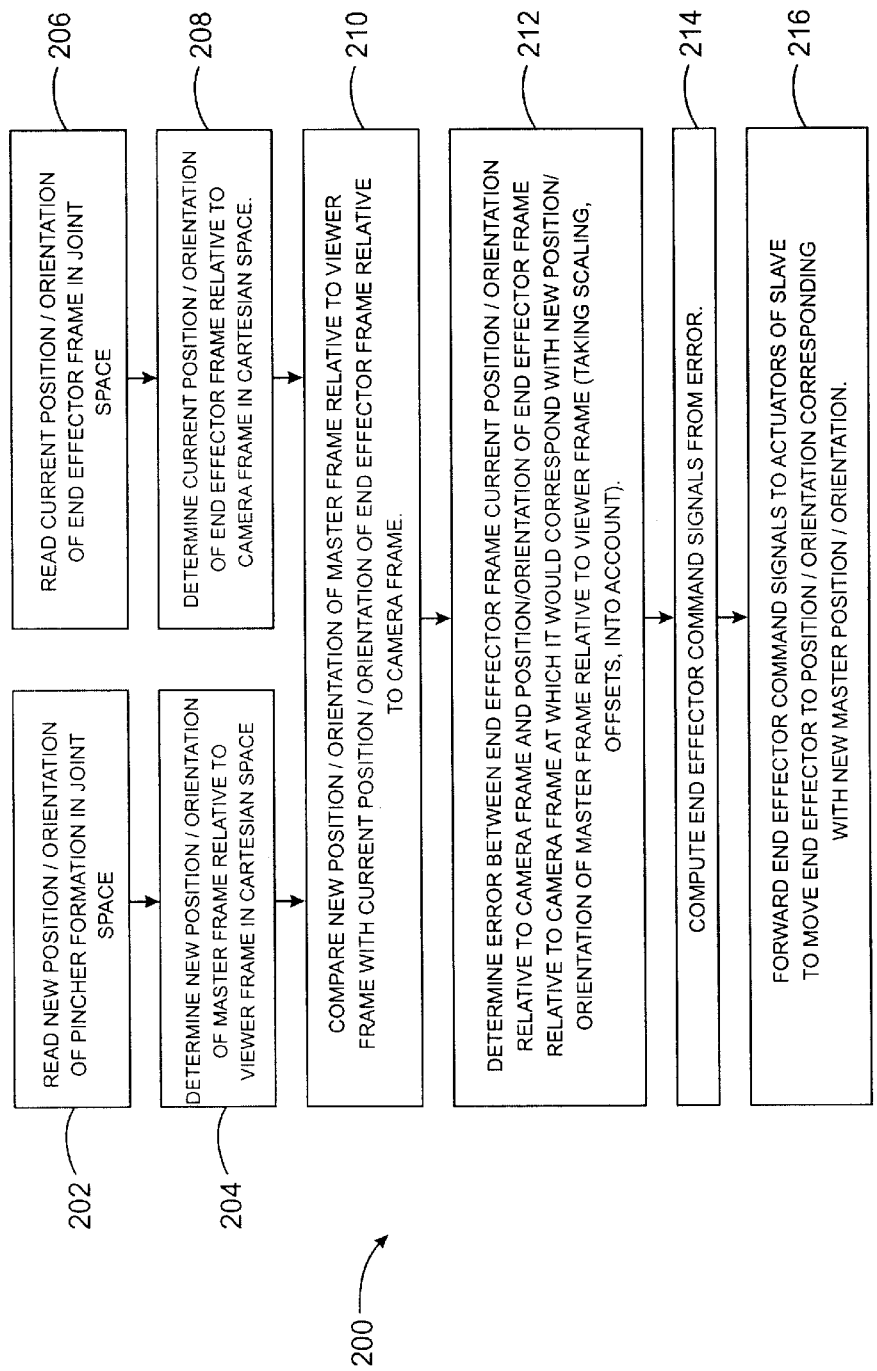
FIG. 10 shows a block diagram indicating control steps of a control system of the surgical system, the control system being arranged to effect control between master control device input and corresponding surgical instrument movement output.

Referring now to FIG. 10 of the drawings, a control system employed to cause the slave to track master input is generally and schematically indicated by reference numeral 200. The control method as indicated by reference numeral 200 assumes that the master and slave were at corresponding positions and the master has been moved into a new position and orientation. Accordingly, since the new position and orientation of the pincher formation 86 relative to the eye frame 150 no longer corresponds with the position and orientation of the end effector frame 116 relative to the camera frame 110, the end effector 60 is caused to move into a corresponding new position and orientation relative to the camera frame 110 at which it does correspond with the new position and orientation of the pincher formation 86 relative to the eye frame 150.

The new position and orientation of the pincher formation 86 is read in joint space as indicated by reference numeral 202. This is achieved by the processor by means of the sensors operatively associated with the joints on the master. From this joint space information, which determines the joint positions of the master, a corresponding new position and orientation of the master frame 158 relative to the eye frame 150 is determined in Cartesian space as indicated by reference numeral 204. In similar fashion, the current position and orientation of the end effector 60 in joint space is read as indicated by reference numeral 206. From this information the current position and orientation of the end effector frame 116 relative to the camera frame 110 in Cartesian space is computed, as indicated by reference numeral 208. The new position and orientation of the master frame 158 relative to the eye frame 150 in Cartesian space is then compared with the current position and orientation of the end effector frame 116 relative to the camera frame 110 as indicated at 210. An error between the end effector frame 116 current position and orientation relative to the camera frame 110 and the position and orientation of the end effector frame 116 relative to the camera frame 110 at which it would correspond with the new position and orientation of the master frame 158 relative to the eye frame 150 is then computed, as indicated at 212.

It will be appreciated that master orientational and positional movement variation need not necessarily correspond proportionally with responsive end effector orientational and positional movement variation. Accordingly, the system is typically arranged to provide for scaling so that the translational movement of the end effector in response to translational movement input on the master is scaled e.g., at a ratio 1 to 2, or the like.

From the error, corresponding end effector command signals are computed as indicated at 214. The end effector command signals are then forwarded to the slave actuators to cause them to move the end effector 60 to a new position and orientation relative to the camera frame 110 at which it corresponds with the new master position and orientation relative to the eye frame 150, as indicated at 216. For further detail, refer to the Ser. No. 09/373,678 application mentioned above.

A method and system whereby auxiliary information related to a surgical procedure to be performed by the system 10 can be selectively displayed on the viewer 14, together with an image of the surgical site captured by the endoscope 24, so as to enable the surgeon selectively to reference such information on the viewer 14 during the performance of the surgical procedure, in accordance with the invention, will now be described.

By displaying auxiliary information related to the surgical procedure in the image of the surgical site displayed at the viewer 14, the surgeon is able to reference such information without having to look at another source or display. For example, by displaying a patient's ECG signal in the image together with the image of the surgical site captured by the endoscope 24, the surgeon need not transfer his direction of view to a location removed from the image of the surgical site. This enables the surgeon to perform the surgical procedure with greater ease and confidence and with less distraction. Furthermore, the surgeon can prepare preoperative information specific to the surgical procedure to be performed, or specific to the patient on which the surgical procedure is to be performed, so as to enable the surgeon selectively to access such specific auxiliary information in the displayed image during the performance of the actual surgical procedure. When displaying the auxiliary information together with the image of the surgical site captured by the endoscope is referred to in this specification, such a description is to be interpreted to have a wide meaning including, for example, displaying the image in a discrete window overlaid on the image of the surgical site, displaying the auxiliary information so as to be merged with the image of the surgical site, such as merging a preoperative x-ray image with the image of the surgical site so that the surgeon can view hidden detail of the surgical site, displaying the auxiliary information selectively on the viewer instead of the image of the surgical site so that the surgeon is presented with an unobstructed view of the surgical site when performing the surgical procedure, the auxiliary information then being selectively displayable in the image at the viewer alternately with the image of the surgical site, and the like. It will be appreciated that the auxiliary information can be displayed on a separate image display or viewer where appropriate.

Figure 11:
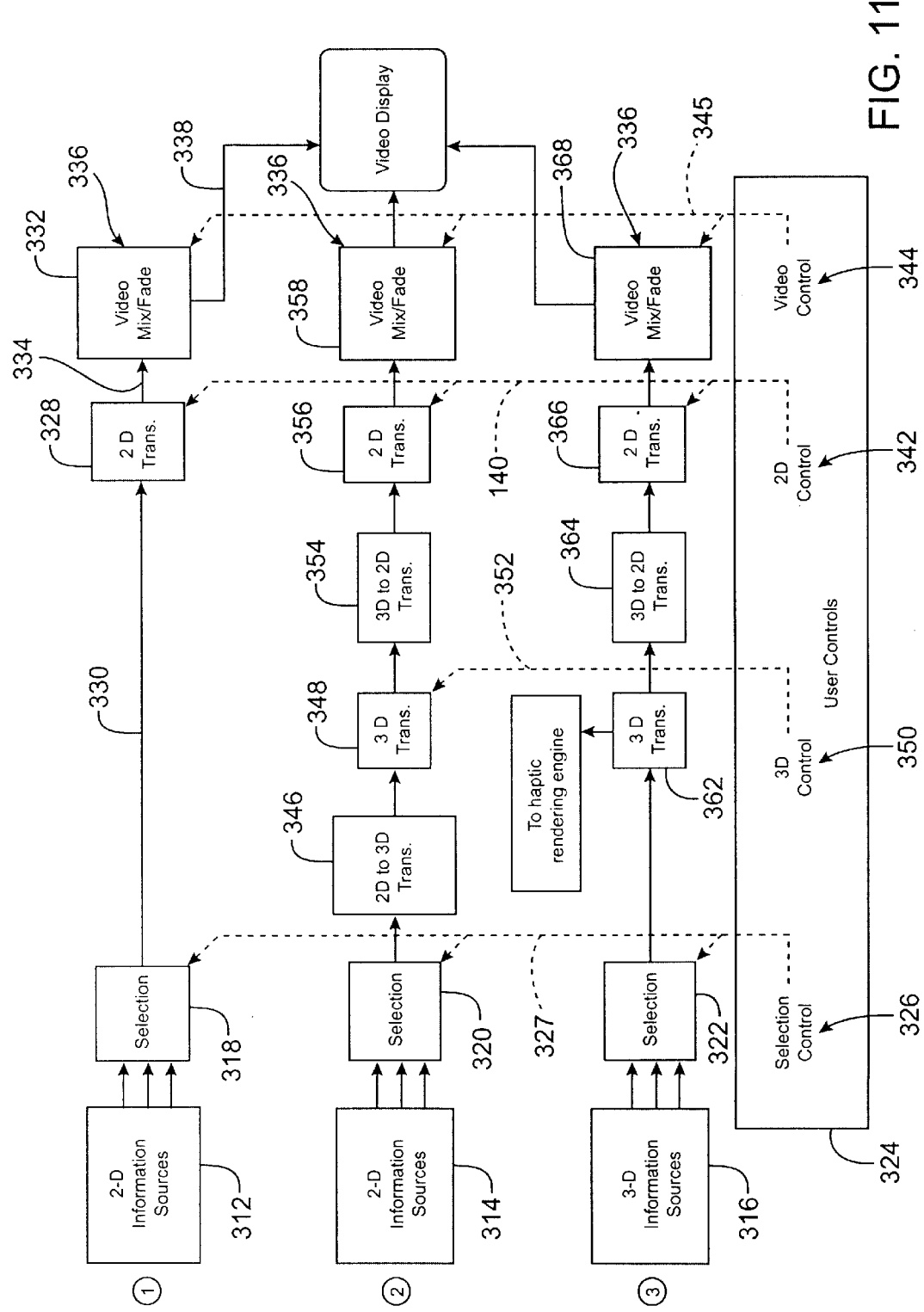
FIG. 11 shows a flow diagram indicating control steps of a method, in accordance with the invention, whereby an operator of the telesurgical system can selectively access one or more sources of auxiliary information related to a surgical procedure to be performed by the telesurgical system, so as to display the information from the selected source or sources on an image display of the telesurgical system together with an image of the surgical site captured by an image capturing device, such as an endoscope, of the system.

Referring to FIG. 11 of the drawings, a plurality of sources of two-dimensional information is generally indicated by reference numeral 312. Another plurality of sources of two-dimensional information is generally indicated by reference numeral 314.

The sources of two dimensional auxiliary information at 312 define auxiliary information to be displayed in the image at the viewer 14 and which is of a type which, when displayed in the image, is to be adjustable to vary its displayed position relative to the image of the surgical site captured by the endoscope. The imaged information from 312 is typically adjustable relative to the image of the surgical site in two dimensions only. Accordingly, the position of the imaged information can be varied to change its position across the image of the surgical site.

If the imaged information from 312 is displayed in a window overlaid on the image of the surgical site, the size of the window is typically also adjustable in two dimensions. The types of information selectively accessible from the sources 312 include, for example, a prerecorded streaming video of the surgical procedure to be ,performed so that the operator can follow the procedure as depicted in the video while displayed in the image at the viewer 14 together with the image of the surgical site. The types of information can further include, for example, a real time ECG signal so that the surgeon can monitor the patient's heart beat within the displayed image at the viewer 14.

Another type of auxiliary information can be in the form of a previously captured and stored image from the endoscope of the surgical site, wherein the pre-captured image was taken to provide a generally panoramic view of the surgical site and the surrounding scene. Such a pre-captured panoramic image can be obtained by the endoscope 24. In such a case, the image can be captured when the viewing end of the endoscope 24 is relatively far removed from the surgical site. After the panoramic image or view is captured in this fashion, the endoscope can be moved such that its viewing end is closer to the surgical site so as to obtain a more suitable real time image for use in the performance of the actual surgical procedure.

It will be appreciated that images other than a panoramic image of the surgical site and surrounding scene can be provided for selective reference on the image display at the viewer 14. Such other images can include, for example, generic or patient specific anatomical images for aiding the operator, or surgeon, for example, in identifying structures so as to determine the surgical site location relative to the patient anatomy. Furthermore, such images can include, for example, images showing the location of the entry ports, or incision points, the position of the surgical instrument shafts and/or the end effectors so as to provide the operator with visible information relating to the location of surgical instruments, or parts thereof. Such image can be computer generated where appropriate, or can be obtained from additional image capture devices, and/or the like. This can be useful to avoid collisions between the instrument shafts, for example. Furthermore, this can provide the operator with visible information enabling him to perceive how the instruments are interacting with each other and/or the patient, in addition to the real time image of the surgical site used to perform the actual surgical procedure. When this information is selected, the auxiliary information can be displayed, where appropriate, to surround or abut a generally closer view of the surgical site captured continually, or in real time, by the endoscope and which is used by the surgeon to monitor and control the surgical procedure. In this manner the surgeon, or operator, can be provided with the real time image from the endoscope at a preferably generally centrally disposed location in the viewed image, while the pre-captured, or real time, auxiliary image, e.g., a more panoramic view of the surgical site and surrounding scene, is displayed along the periphery of the real time image obtained from the endoscope 24. This can serve to provide the operator with a better idea of where he or she is operating relative to the area surrounding the surgical site. Instead of providing the auxiliary image to surround the real-time image of the surgical site, the auxiliary image can be displayed in a discrete window, or in a "picture in picture" arrangement, extending over the image of the real-time surgical site image. As another alternative, the auxiliary image can be displayed alternately with the actual real-time image. Thus, during the performance of a surgical procedure, the surgeon can intermittently switch between the image of the real-time surgical site image and the auxiliary image by means of any appropriate switching input device or method, such as, buttons, switches, voice command, and/or the like. When the information from 312 is displayed in a window overlaid on the image of the surgical site, the surgeon can typically vary the size of the window and place the window relative to the image of the surgical site so that the information is presented at a location which is comfortable to the surgeon and at which the window does not obstruct important detail of the surgical site image.

By way of example, a specific application of such a "picture in picture" arrangement will now be described. During the course of a surgical procedure, the displayed image of the surgical site is typically in the form of a "narrow" field of view image normally being live, e.g., continually updated, magnified and focused particularly on the surgical site. Such a "narrow" field of view typically provides the operator with a large image of a relatively small area in the patient. Such a "narrow" field image is typically captured in real time by means of the endoscope 24. It has been found advantageous to provide the operator with a "wide angle" image of the surgical site and surrounding scene, to assist the operator in determining where the surgical site and surgical tools are with reference to the surrounding scene. Such a "wide angle" image can be in the form of a "still" image captured by the same endoscope at a position further removed from the surgical site than at which it is normally positioned when capturing the real time image used by the operator as he or she performs the surgical procedure. Instead, the "wide angle" image can be captured in real time by another image capture device, or endoscope, or the like. The two images can be displayed in a variety of different ways. In one way, the "wide angle" image can be displayed in a "smaller" window and the "narrow" field image can be displayed over a relatively larger area. The surgeon can then refer to the "smaller" window for referencing orientation, or the like. In another way, the "narrow" field image is displayed in a "smaller" window and the "wide angle" image is displayed over a relatively "larger" area to provide context to the surgeon to help him or her to remain oriented at the surgical site.

It can happen that the surgeon wishes to change the image displayed on the viewer 14. This can be achieved, e.g., by rotation of the endoscope 24 relative to the site viewed. Where the "wide angle" image is a "still" image, this image can be caused to rotate together with rotation of the "live", magnified image. This can be achieved by causing the "still" image to be modified, for example, by means of computer control, so that the "still" image rotates to the same degree as the "live" image, so as to maintain, for example, context for the surgeon should the surgeon desire to rotate the endoscope during surgery. In addition, or instead, if the surgeon desires to pan with the endoscope, the "still" image can be modified so that the "still" image preserves alignment, or registration, with a corresponding part of the "live" image.

The sources of two dimensional auxiliary information at 314 define auxiliary information to be displayed in the image at the viewer 14 and which is of a type which, when displayed in the image, is to be adjustable to vary not only its two-dimensional displayed position relative to the image of the surgical site captured by the endoscope, but also its displayed orientation in three dimensions relative to the displayed image of the surgical site. One of the sources at 314 can contain preoperative information which is to be aligned or brought into register with the image of the surgical site. For example, a two dimensional CAT scan image of a surgical site particular to the patient on which the surgical procedure is to be performed can be obtained preoperatively and loaded into one of the sources at 314. Such a preoperative image can be obtained so as to correspond with an image to be captured by the endoscope, in other words, an image corresponding to the image which the endoscope is to capture during the surgical procedure from a specific vantage point. Instead, the preoperative image can be from a vantage point different to that of where the endoscope is to be during the surgical procedure. During the surgical procedure, the surgeon can then access the CAT scan information from the particular source at 314 and place it in the displayed image of the surgical site. Such an image can then be adjusted in three dimensions so as to bring the preoperative CAT scan image generally into register with the image of the actual surgical site captured by the endoscope. Since the information from the sources 314 represent two dimensional information, there may be a limit to the amount of orientation change that can be tolerated before the information ceases to be of use to the surgeon.

Still referring to FIG. 11 of the drawings, a plurality of sources of three-dimensional information is indicated at 316. One of the sources can include, for example, a three-dimensional model corresponding to a surgical site on which a surgical procedure is to be performed. Such a three-dimensional model can be, for example, raw volumetric images, such as point cloud or voxel representations, or the like, a computer generated three-dimensional model or image, a segmented three-dimensional model obtained from CAT (Computer Aided Tomography) scans, MRI (Magnetic Resonance Imaging) techniques, or the like. During the surgical procedure, the surgeon can then access the model and place it in the image of the surgical site. The image corresponding to the auxiliary information in the form of the three-dimensional model, can typically be superimposed, or merged, with the image of the surgical site. The brightness of the image of the three-dimensional model is typically adjustable so as to cause it selectively to fade relative to the actual image of the surgical site.

Once placed in the image, the image of the model can be positionally and orientationally adjusted, and typically scaled, so as to enable the surgeon to bring the preoperative image into register with the actual image of the surgical site. Should the position of the endoscope be changed, for example, to obtain an image of the surgical site from a different vantage point, the registration of the preoperative image can be made to remain in register with the surgical site. This can typically be accomplished by causing the control system of the surgical system 10 to fix the position of the preoperative image relative to a suitable reference frame once the surgeon has brought the preoperative image generally into register in the displayed image. A suitable reference frame can be, for example, a reference frame attached relative to the cart 20, or the patient, or the like. Since registration is often effected visually by the surgeon, it may be that the registration is not entirely true or accurate. Thus, should the endoscope position be moved to capture an image of the surgical site from a different vantage point, it may be that the surgeon may again have to perform a slight adjustment to the registration should the preoperative image not be correctly registered with the actual image of the surgical site upon changing the endoscope position. Instead of manual registration as described above, automatic registration of the preoperative image with the surgical site image can be achieved in accordance with known imaging techniques. Advantageously, registration can be accomplished by enabling the surgeon, or operator, to perform an initial manual registration procedure, followed by an automatic registration procedure in accordance with conventional methods, to achieve a truer registration. Although reference has been made to a model, it will be appreciated that other auxiliary information can be used instead. Such other auxiliary information can include preoperative images as well as inter-operative images. For example, an inter-operative image, or preoperatively obtained model, and/or the like, of a beating heart can be registered with the actual image of the beating heart as captured by the endoscope, and/or the like.

Referring again to the two-dimensional information at the sources 312, the two dimensional information can typically be in the form of intrinsically two-dimensional information. Such information can include two dimensional visual images, such as video images, x-ray images, ultrasonic images, and/or the like. These two-dimensional images can be in digital or analog format, or the like. The information can be in the form of static images. Such static images can be in tiff, jpeg, and/or the like, file formats, for example. The information can be in the form of moving images, such as, for example, streaming videos, as already mentioned. Such moving images can be in mpeg, digital video, analog video, such as NTSC or PAL, and/or the like, formats, for example. The information can be textual, numeric, symbolic, and/or graphic in form. For example, the information sources can include sources of information in the form of words, numeric readouts, status icons, bargraphs, stripchart displays, and/or the like. In this manner, for example, representations of blood pressure gauges, heartbeat rate, warning messages, notifications, warning lights, warning icons, or other warning signals related to system status, for example, the time in the form of a representation of a digital or analog clock, e-mail messages, and/or the like, can be displayed. Accordingly, numeric readouts can correspond to blood pressure, heartbeat rate, elapsed and absolute time, and/or the like. Status icons can include icons indicating the status of the system 10, the identification of the type of surgical instruments currently mounted on the robotic arms, and/or the like. Bar graphs can correspond to patient specific information, such as, temperature, oxygen levels in the patient's blood, and/or the like. Bar graphs can also correspond to system specific information such as force magnitude, back-up battery status, and/or the like. Strip charts can correspond to EEG, ECG, blood pressure, and/or the like. Symbolic or graphic representations can correspond to clocks, warning indicators, and icons selectively activatable to provide access to sources of other auxiliary information, such as the three-dimensional and two-dimensional information, described above, menus, web pages and/or the like.

One, or more, of the sources may even comprise a separate computer operatively connected to the system 10. The computer can be a computer on which a surgeon has prepared preoperative information for a specific patient on which a surgical procedure using the system 10 is to be performed. Such a computer may be remote from the system 10. When linked to the system 10 as a source of auxiliary information, in accordance with the invention, the surgeon is able to access such preoperative information on the remote computer from the system 10, so as selectively to display such information on the viewer 14 during the performance of the surgical procedure. Thus, the surgeon, from this source, can access information which may be resident on a computer screen within his or her office, for example.

The images derived from the sources at 312, 314 and/or 316, may be stored images or may be real-time images. Accordingly, the system 10 may include dedicated memory on which the images can be recorded preoperatively if the images are patient or surgical site specific, for example, so as to be stored in resident memory of the system 10. Instead, or in addition, the system 10 can have one or more input connectors, or jacks, to enable the system 10 to be operatively linked to a source of auxiliary information external to the system 10. In this fashion, the system can be linked to an external source of auxiliary information, such as, for example, a remote computer as described above, an ECG source, computer networks such as Local Area Networks (LANS), the internet, and/or the like. Accordingly, it will be appreciated that the sources 312, 314 and 316, can be in the form of resident memory of the system 10, on which memory the auxiliary information is stored, or can be in the form sources external to the system 10, which external sources are connectable to the system 10 through the input connectors or jacks.

Sources of three-dimensional information are indicated at 316. These sources represent information which is intrinsically three-dimensional. Such types of information can include, for example, segmented organ and/or vasculature models, patient specific and/or generic biomedical models, non-biological geometric shapes, markers, and/or the like. Such types of information can also include, for example, real time three-dimensional video, laser scans, and/or the like. Such types of information can yet further include landmarks, identifiers, or other markers that are attached to fixed locations in space. The use of such landmarks, identifiers, or other markers will now be described, by way of example. In the case where the surgeon wishes to perform an anastomosis, for example, he or she can place a landmark, or identifier, or the like in the image displayed on the image display and then move the landmark or marker to correspond with the area where the anastomosis is to be performed. The marker can then be attached to the area so that if the endoscope is moved, for example, the marker remains in a registered condition with the area to which it is attached.

The non-biological geometric shapes are typically used to place visible haptic constraints in the displayed image at the viewer 14. The purpose of placing such haptic constraints in the image is, for example, to inhibit the end effectors from moving beyond such constraints, containing end effector movement within such constraints, and/or the like. Accordingly, the operator of the system can select an appropriately shaped geometric shape, or shapes, and, place it, or them, in the image, and then position the selected geometric shape, or shapes, in the image around an area, or organ, or tissue, for example, so as to protect that area, or organ, or tissue from invasion by the end effectors 60, or to constrain end effector movement to remain within such shape or shapes, miter-box-fashion. Thus, should the site on which it is desired to perform a surgical procedure be close to a sensitive organ, or tissue, or the like, an appropriately shaped geometric shape, or shapes, can be selected, placed in the scene of the surgical site and moved into a position in which the selected shape, or shapes, extend over the sensitive area. When the shape, or shapes, is so placed, a corresponding haptic constraint, corresponding to the selected and placed geometric shape, or shapes, is initialized so as to inhibit the end effectors 60 from trespassing beyond the visible constraint, or constraints, as placed in the image by the surgeon thereby to protect the sensitive tissue, or organ, or the like. The geometric shapes can be of any appropriate shape. Accordingly, such shapes can include, for example, polyhedral shapes, NURBS (Non-Uniform Rational B-Spline), implicit surface shapes, planar shapes such as walls, and/or the like. The geometric shapes can include volumetric shapes such as point cloud, voxcels, and/or the like. The file formats used to store such geometric shapes can be .obj, .dxf, .3ds, VRML, and/or the like, for example. It will be appreciated that once an appropriate selected geometric shape, or shapes, is placed in the image, the surgeon can move the shape, or shapes, into a position covering or shrouding an area of sensitivity. When this has been done, the control system of the system 10 can typically allocate coordinates to the placed shape, or shapes, relative to an appropriate frame, such as a frame attached to the cart 20, or patient, or the like. The system, after having determined the coordinates corresponding to the placed shape, or shapes, then inhibits the end effectors from moving beyond such coordinates or constrains end effector movement to remain within such coordinates. For a more detailed description of a control system of the system 10 whereby such constraints can be imposed, refer to Applicant's co-pending application Ser. No. 09/288,068 filed Apr. 7, 1999 entitled "Aspects of a Control System of a Minimally Invasive Surgical Apparatus". Geometric shapes can also be used to guide the surgeon or to assist in finding locations of particular interest. Furthermore, haptic feedback can be used to indicate information about objects which may not be readily discernable visually. For example, sensitive areas can be given repulsive behavior so that the tools are not only inhibited from approaching the sensitive areas, but are restrained when approaching the sensitive areas at a predetermined distance from such areas.

Such geometric shapes can be provided with geometric description or additional information, and can contain information about appearance, e.g., via visual texture mapping, and/or the like, surface and volume properties, e.g., such as mass, density, impedance, and/or the like, in accordance with known methods in the field of haptics. The shapes can also be derived from biological sources such as segmented MRIs. Such additional information about geometric shapes can be used for visual representation, e.g., colors, patterns, textual maps, flashing appearances, and/or the like. Such additional information can also be used with haptic rendering to provide, for example, stiffness, artificial friction, masses, vibrations, or other physical or non-physical force cues.

The various sources of information as indicated at 312, 314, and 316, are typically represented as icons on the display area of the video display 14. Accordingly, the operator of the system can select any one or more of the desired sources by selecting the appropriate associated icon. The step of selecting the desired source of auxiliary information is indicated by the blocks 318, 320, and 322 for the sources at 312, 314, and 316, respectively. Selection of a desired source typically takes place at the operator console 12. Such selection can be made in any appropriate manner, such as by using buttons, foot pedals, a mouse, and/or the like, for example. Advantageously, such selection is made by making use of one, or both, or either of the master controls 70, 70. In such a case, one, or both, or either, of the masters 70, 70 can serve as a two-dimensional or three-dimensional mouse. Accordingly, one, or both, or either, of the masters can be arranged to perform functions relative to the displayed image in a manner analogous to a conventional mouse relative to a computer screen. Therefore, one, or both, or either, of the masters can be arranged to perform functions such as to point, highlight, move, select, and/or the like.

The masters each typically have at least six degrees of freedom of movement. Accordingly, when used as a three-dimensional mouse, such master can be arranged to control six variables, for example. Therefore, functions such as, shifting, rotating, panning, tilting, scaling, and/or the like, can be performed simultaneously when one, or both, or either, of the masters are used as a three-dimensional mouse, without another input being required. In particular, for two-handed or two-master operation, any windows or overlays can be handled as "elastic" bodies, such that resizing, scaling, warping, and/or the like, can, for example, be controlled by pulling the masters apart, or the like. In this manner, the selected auxiliary information when displayed in the display image of the viewer 14 can be positionally and orientationally adjusted in three-dimensions in a three-dimensional environment, where appropriate, or where desired. The masters 70, 70 are typically provided with force feedback. The force feedback on the masters 70, 70 can be arranged to provide functions related to auxiliary information selection, placement, orientational and positional movement, for example, to draw, or "suck", the masters to an icon when an associated cursor is within a predetermined area around the icon, and/or the like. Refer to Applicants co-pending U.S. patent application Ser. No. 09/398,507, entitled "Master Having Redundant Degrees of Freedom," filed Sep. 17, 1999, the full disclosure of which is incorporated herein by reference, for further information in connection with master control. Whatever method and/or device used to make such selection, the selection step is indicated in the block 324 at 326 and as indicated by the dashed lines 327. It will be appreciated that the block 324 represents selection and regulation steps that are performed by means of the appropriate inputs, such as the master control devices 70, 70, at the surgeon's console 12 by the operator.

The steps whereby the information from the information sources 312 is selected and then presented or placed in the image at the video display will now be described in greater detail.

As mentioned, the selective placing of the auxiliary information from the sources 312 can be selectively caused to be displayed to extend at least partially across an image display area of the viewer 14, such as in a localized window. When displayed on the display area, the position at which the information is displayed relative to the display area can be regulated or changed by the operator in two dimensions. Once a desired source is selected by the operator by operation of an appropriate input at 326, the desired source is selected at 318. The information from that selected source is then forwarded to a two-dimensional transform indicated at 328, as indicated by arrow 330. After the two-dimensional transform step at 328, the information is fed to a video mix and fade step at 332, as indicated by arrow 334. At the block 332, the information from the selected source at 312 is mixed with the video image captured by the endoscope 24. The video image captured by the endoscope 24 is indicated by arrow 336. When the information from the selected source at 312 is thus mixed with the image captured by the endoscope 24, the combined images are forwarded to the video display as indicated by arrow 338 so that both images are placed in the image at the viewer 14.

Figure 12:
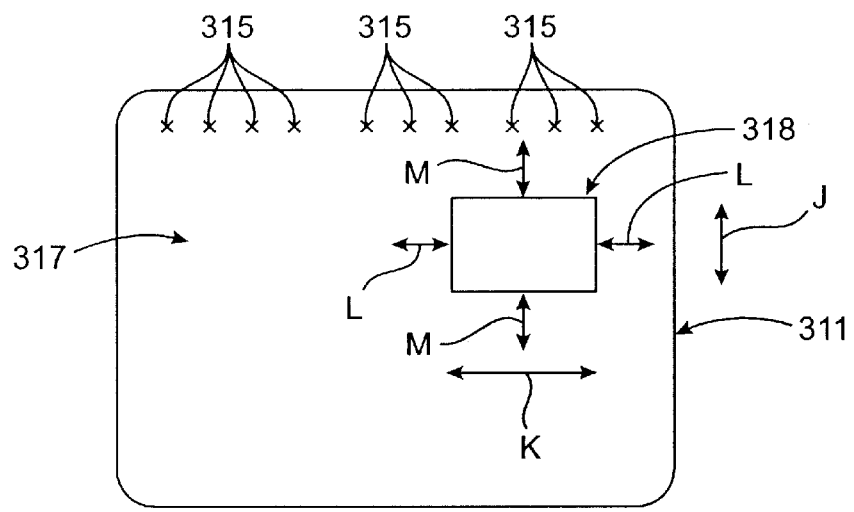
FIG. 12 shows a schematic view of an image of a surgical site displayed on the image display of the telesurgical system and further shows an image corresponding to auxiliary information from a selected source of auxiliary information displayed in a window overlaid on the image of the surgical site.

Referring to FIG. 12 of the drawings, an image comprising a combination or merger of the image from the endoscope and the selected source at 312 is indicated generally by reference numeral 311. An image derived from the source at 312 is indicated at 318, and is shown as being overlaid on the image from the endoscope indicated at 317. A row of icons is indicated by reference numerals 315. The source at 312 was selected by actuating a corresponding one of the icons 315.

Referring again to FIG. 11, and as indicated by the dashed line 140, the surgeon or operator of the system 10 can regulate the two-dimensional transform at 328, as indicated at 342. This can be achieved in any appropriate manner, such as through appropriate input devices such as, for example, buttons, toggles, joysticks, mice, and/or the like. Advantageously, one, or both, or either, of the master control devices 70, 70 are used as the input device or devices whereby the two-dimensional transform 328 can be regulated. The representation of the combined images can be presented such that the information from the selected source 312 is cropped in a localized window, as indicated in FIG. 12 of the drawings, in the image displayed at the viewer 14. Accordingly, the image 317 captured by the endoscope 14 is positioned to extend across at least a major part of the display area, the information from the selected source at 312 being positioned in a localized window overlaid on the image captured by the endoscope 24. By manipulation of the input at 342, the two-dimensional transform at 328 is regulated to cause the window displaying the information from the selected source at 312, to be moved relative to the rest of the image, and to be placed where desired by the operator, as indicated by arrows J and K in FIG. 12. Typically, the size of the window can be varied, as well as its position relative to the rest of the image, as indicated by arrows L and M.

The video mix and fade step 332 is also regulatable by, for example, the operator at the operator console 12, or by another person, at a different location, if appropriate. An appropriate input for performing such regulation is indicated at 344 and is operatively connected as indicated by the dashed lines 345 to the video mix and fade block at 332. By manipulation of the input at 344, the information from the source at 312 can be faded relative to the image from the endoscope 24. Advantageously, the input at 344 is also performed by means of one, or both, or either, of the master controls 70, 70.

Referring now to the information sources at 314, these sources provide two dimensional information which, when displayed on the display area at the viewer 14, can be regulated so as to change the position of such information relative to the display area at the viewer in three dimensions, as described in greater detail herein below.

An appropriate one of the sources of two-dimensional information at 314 can be selected in similar fashion to the selection of one of the sources at 312. Accordingly, the operator can select information from a desired source at 314 by manipulating the appropriate input at 326. The selection step is indicated at 320. Once selected, the information from the desired source is forwarded to a two-dimensional to three-dimensional transform indicated at 346. At the step 346, the two-dimensional information from the selected source at 314 is converted to a three-dimensional representation. It is then passed through the three-dimensional transform indicated at 348. The three-dimensional transform at 348 is regulatable by the operator as indicated at 350 and by the dashed line 352. This can typically be achieved by means of any one or more of the inputs mentioned above. However, advantageously, the appropriate input is one, or both, or either, of the master controls 70, 70. By means of the input at 350, typically the position, orientation and scale of the two-dimensional information from the selected source at 314, can be regulated to change its position, orientation and scale in three dimensions. It will be appreciated that, in this fashion, not only the position, but also the orientation of the two-dimensional image as displayed in the image as viewed at the viewer 14 can be changed.

Once the operator has regulated the two-dimensional information by means of the three-dimensional transform at 348, the information is passed to block 354, where the information is transformed from a three-dimensional representation into a two dimensional representation. The two-dimensional transform is indicated at 356. The two-dimensional transform is regulatable by the operator through the input 342 so as to change the position of the information, as displayed in the image at the viewer 14, in two dimensions. It will be appreciated that this corresponds to changing the position of the image of the auxiliary information from the source at 314 relative to the image of the surgical site. After regulation at 356, the information is passed to a video mix and fade block at 358, where it is mixed with the image from the endoscope 24 as indicated by arrow 336. As in the case with the video mix and fade block 332, the operator can cause the information to fade relative to the image captured by the endoscope 24 by means of the input at 344. The image 336 from the endoscope 24 is combined with the information from the selected source at 314 and is then forwarded to the viewer 14 to be displayed thereon.

Figure 13A:
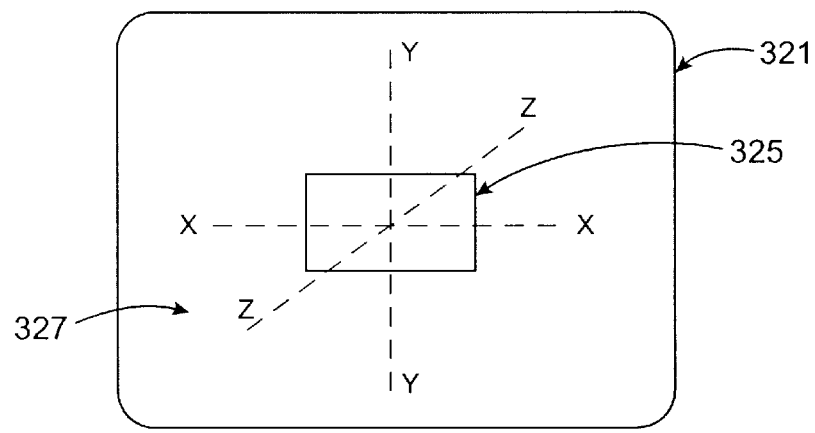
FIGS. 13A and B show schematic views illustrating the adjustment in position and orientation of an image corresponding to auxiliary information from a selected source of auxiliary information, relative to an image of the surgical site from an image capturing device.

Referring to FIG. 13A of the drawings, an image comprising a combination or merger of the image from the endoscope and the selected source at 314 is indicated generally by reference numeral 321. An image derived from the source at 314 is indicated at 323 and is shown as being overlaid on the image from the endoscope indicated at 327. As in the case with reference to FIG. 12, and as can best be seen in FIG. 13B of the drawings, the image from the source 314 can be repositioned with reference to arrows J and K and can be adjusted in size as indicated by arrows L and M. This is achieved by the operator of the system 10 at 342 by means of the transform at 356 as indicated by dashed line 140.

Figure 13B:
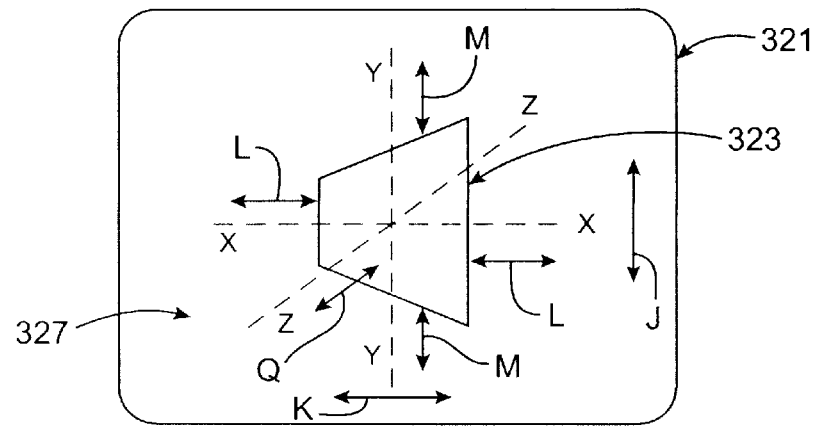

In addition, and with specific reference to FIG. 13B of the drawings, the image from the selected source at 314 is orientationally adjustable or regulatable. Accordingly, the image from the selected source 314 can be regulated so as to change its orientation in three dimensions with reference to the arbitrary reference frame indicated in dashed lines in FIG. 13A. Although in FIG. 13B the image from the source 314 is shown as having been adjusted angularly about an arbitrary y axis with reference to the reference frame in FIG. 13A, it will be appreciated that angular adjustment about the x and z axes can be performed in similar fashion. Such angular regulation of the image from the selected source at 314 is achieved by the operator of the system 10 at 350, so as to regulate the information from the selected source at 314 by means of the transform at 348 as indicated by dashed line 352. In similar fashion, the image can also be moved "inwardly" and "outwardly" as indicated by arrows Q along the z-axis.

Referring now to the three-dimensional information sources 316, informations from one or more of the sources can be selected by the operator by means of the input 326 and as indicated by the block 322. The three-dimensional information from the selected source at 316 is then passed to a three-dimensional transform as indicated at 362. The operator, by using the input device at 350, can then regulate this information in the three-dimensional transform at 362 so as to vary typically the orientation, position and scale of an image derived from the selected source and as displayed at the viewer 14 in similar fashion as described above with reference to FIGS. 13A and 13B. Once the information has been regulated in this fashion, the information is forwarded to a block 364 where the three-dimensional information is transformed from three dimensions to two dimensions. The resultant two-dimensional information is then forwarded to a two-dimensional transform at 366. The information can then again be regulated by the operator by means of the input device at 342 as herein before described with reference to the two-dimensional transforms 328, 356. As before, the resultant information is then fed to a video mix and fade block as indicated at 368 where the information is mixed with the image from the endoscope and is then passed to the viewer. Where appropriate, the information can be caused automatically to register with a corresponding surgical site image captured by the endoscope, as already described herein above. Instead, as described above, registration can be manual only, or a combination of manual and automatic methods.

It will be appreciated that the above methods can be used with two-dimensional single channel video display or with three-dimensional dual channel video display. In the latter case, the real time video source 336 can comprise two separate images for "right" and "left" channels for viewing by the right and left eyes of the surgeon. Elements 354 and 364 can then provide two separate images from two distinct viewpoints for the right and left channels respectively. The subsequent elements, or steps, can then be applied to both channels. Furthermore, element 328 can be arranged to duplicate the signal 334 into a left and a right channel and to shift them relative to each other to place the original two-dimensional image in a three-dimensional viewer at variable apparent depths.

Advantageously, at least one of the master controls is operatively arranged to fulfill some, preferably all, of the functions in the block 324. Accordingly, the operator need then not remove his hands from the master control devices 70, 70 when selecting and changing the position, orientation and scale of the auxiliary information when displayed in the image at the viewer 14. In this way, continuity of control of the surgical procedure is enhanced whilst still enabling the operator to access and place auxiliary information from one or more of the sources 312, 314 and 316.

As already mentioned, the masters 70, 70 are normally operatively associated with the slaves. Typically, when one, or both, or either, of the masters are to be used selectively to place an image corresponding to auxiliary information from a selected source 312, 314, 316 in the image or scene of the surgical site, the operative association between the master, or masters, and the slaves is temporarily interrupted. When this occurs, the slaves are typically held or locked in stationary positions at the surgical site. Accordingly, the slaves are locked in the positions they occupied immediately before disassociation with the masters 70, 70. The master or masters are then freed to enable them to be used to select and place the desired auxiliary information in the scene or image of the surgical site captured by the endoscope 24 and displayed across the display area of the image display or viewer 14. Once the auxiliary information has been selected and placed, operative association between the masters 70, 70 and the slaves is re-established to permit the operator to proceed with the surgical procedure with reference to the auxiliary information now displayed on the display area of the viewer 14 after having been selected and placed in the scene by means of one, or both, or either, of the masters 70, 70. Refer to Applicant's co-pending U.S. patent application Ser. No. 09/398,960, entitled "Repositioning and Orientation of Master/Slave Relationship in Minimally Invasive Telesurgery," filed Sep. 17, 1999, the full disclosure of which is incorporated herein by reference, for a more detailed explanation of how the operative association between the masters and the slaves is preferably reestablished.

When one of the masters is used to select the desired auxiliary information, a cursor is typically generated in the image upon disassociation with the slaves. The cursor is then guided by movement of the master until the cursor is over the desired icon 315. The master is then also typically used to actuate the icon to cause the desired auxiliary information to be accessed and placed in the image of the surgical site. Advantageously, this can be achieved by squeezing the pincher formation 86, "pressing" the icon, or the like. When placed, the master, or both masters, is then used to vary the position and/or orientation of the image corresponding to the selected auxiliary information relative to the image of the surgical site as described above, and where appropriate. One or both masters may be used to vary the position and orientation of auxiliary information, overlays and windows in a manner similar to the way in which masters are used to vary the position and orientation of an image from an image capture device as described in co-pending application entitled "Image Shifting Apparatus and Method for a Telerobotic System," previously incorporated herein by reference. Of course, the present invention also encompasses other manners of manipulating auxiliary information, in addition to the preferred masters disclosed, such as by repositioning/rotating a joystick, using multiple input buttons to indicate the desired manipulation, or using a voice control/recognition system to command the system to manipulate the auxiliary information as desired.

Should, during the course of a surgical procedure, an image capture device generating a real time video image 336 be moved, the image displayed on the image display may be caused to shift and/or rotate in response to such image capture device movement. Instead, the video image 336 can be caused to shift/rotate electronically, for example. During such a change in the displayed real time image, the two-dimensional and three-dimensional transforms 328, 348, 354, 356, 362, 364, 366 can be arranged to synchronize their operation with the change in the displayed image so as to cause the auxiliary information to appear attached to the displayed real time image. Instead, the transforms can be arranged to ignore the change in the displayed real time image to cause the auxiliary information to appear attached to the image display and to drift relative to the changing real time image.

Figure 14:
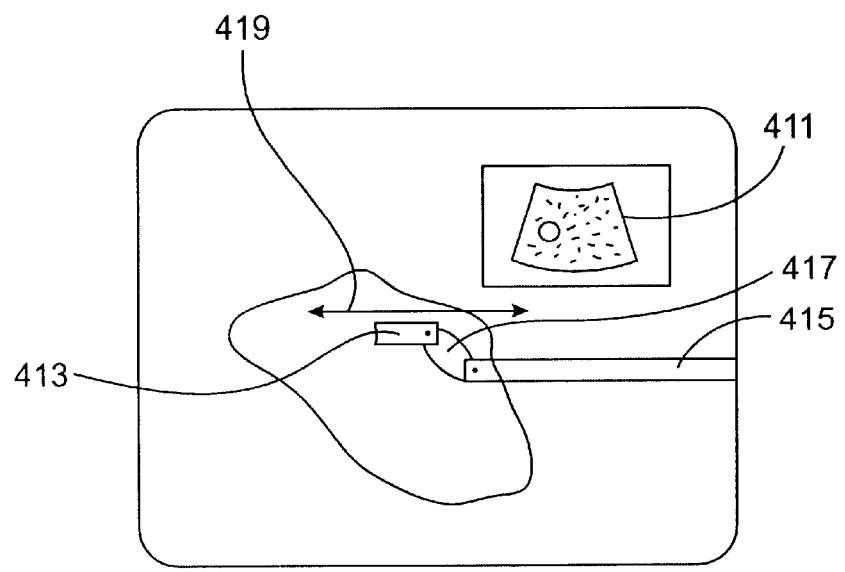
FIG. 14 shows a schematic diagram of an image displayed at a viewer of the system shown in FIG. 1, and further shows a probe gathering auxiliary information relating to a surgical procedure.

Another source of auxiliary information will now be described with reference to FIG. 14. Such a source of auxiliary information can typically include an appropriate image gathering device such as one including a transmitter and receiver arrangement, as schematically indicated at 413. An example of such a device is an ultrasound transducer which will be used by way of example only in the description which follows. Accordingly, the invention is not to be limited to an ultrasonic device. Any appropriate device which can gather similar information falls within the scope of the invention. Such a source can be used to obtain a preoperative or intraoperative two-dimensional or three-dimensional image, or model, corresponding to a surgical procedure to be performed. Accordingly, it can be either a two-dimensional source 312, 314 or a three-dimensional source 316 depending on its application. As a two-dimensional source, the ultrasonic transducer can be used to obtain a single ultrasound image. As a three-dimensional source it can be used to obtain a plurality of spaced ultrasonic images, or cuts, thereby to provide sufficient information for construction of a three-dimensional model. Accordingly, it can be arranged to move, or sweep, across a surgical site to capture such images, or cuts. This can typically be achieved, for example, in accordance with a pre-programmed sequence for moving the ultrasound transducer, manual movement of the ultrasound transducer, or the like. The ultrasonic transducer can be mounted at an end of a shaft to enable it to be introduced to the surgical site through a relatively small aperture, in a minimally invasive manner. The sweeping movement can be performed manually by moving an opposed end of the shaft positioned outside the body. To this end, a handle can be provided on the opposed end of the shaft. Conveniently, manually operable actuators can be provided at the handle to enable the ultrasonic transducer, or probe, to be moved relative to the end of the shaft on which it is mounted by manipulating the actuators. Instead, the shaft can be mounted on a robotic arm, the movement being controlled through a master control device. In another embodiment, the movement of the ultrasonic transducer can be controlled by means of a computer program. Accordingly, whether performed manually or automatically, a plurality of separate images can be obtained and used to form a "mosaiced" surface of images in a fashion similar to that known in the satellite and undersea imaging industries, namely, by "painting" the sensor, or ultrasonic transducer, across the surface being viewed. Said surface of images may be intrinsically two- or three-dimensional in nature depending on the movement of the sensor during the build-up of the image. A different series of image "slices" may be constructed from a sensor that produces a planar image and that is moved substantially normal to the image plane to produce a series of slices, as is known, for example, in prenatal ultrasonic imaging practice. Taken together, these form an intrinsically three-dimensional or volumetric image.

These built-up two- and three-dimensional images may then be introduced into the system to be selectively overlaid and positioned within the surgeon's field of view at the viewer. As can best be seen in FIG. 14, such an ultrasonic image, when in a two-dimensional format, may be displayed as indicated by reference numeral 411.

Such a source can also be used inter- or post-operatively. For example, it can be used as a flow probe, or the like, to enable the surgeon, for example, to ascertain the degree of fluid flow through a vessel, or the like. In such a case, when, for example, an anastomosis procedure has been performed, a surgeon, or operator, of the system may wish to determine whether or not the anastomosed vessels are allowing sufficient blood flow therethrough, whether or not one or more of the vessels has been damaged during the procedure so as to require further corrective surgery, and/or the like. The flow probe, or ultrasonic transducer, can then be used to establish this.

Advantageously, the ultrasonic transducer, or other appropriate device, or flow probe, can be mounted on an end of a shaft 415 to permit it to be introduced into a patient body in similar fashion to the surgical instruments 28, in a minimally invasive manner. Conveniently, the ultrasonic transducer can be mounted on an end of the shaft by means of a wrist member 417 similar to the wrist member 52, or more than one wrist member, which cooperate with each other, to enable it to be angularly displaced relative to the shaft in similar fashion to the end effector 60, in multiple degrees of freedom of movement. The mounting of the ultrasonic device on the end of the shaft 415, whether by means of one or more wrist members, or otherwise, is preferably such as to provide the ultrasonic device with relatively large sweeping movement capability relative to the end of the shaft, as indicated by arrows 419. Accordingly, it can have a relatively large lateral range of motion although narrow ranges of motion, or none at all, relative to the end of the shaft, fall within the scope of the present invention. Movement of the ultrasonic device relative to at least the end of the shaft is preferably controlled from outside the patient body, in use. For example, actuators positioned remote from the end on which the ultrasonic transducer is mounted may be used to control movement of the ultrasonic device relative to the end of the shaft from outside the patient body. Instead, or in addition, actuators can be provided to cause the ultrasonic transducer to scan an area of interest. The shaft may have a handle at its proximal end, opposed from the flow probe, for manual control by means of manually controllable actuators, or it may be mountable on a robotic arm as described above for control by means of a master control device. Accordingly, in a preferred embodiment, the ultrasonic device is mounted on a distal end of a robotic surgical tool of the type disclosed in U.S. Pat. No. 5,808,665, entitled "Endoscope Surgical Instrument and Method For Use," the full disclosure of which is incorporated herein by reference. Movement of the ultrasonic transducer across a desired area of interest could then be accomplished by a surgeon or operator of the system 10 by manipulation of a remotely controlled master control at the control station 12 as described in U.S. patent application Ser. No. 09/398,507. Instead, the probe could be arranged to be releasably grasped by a surgical instrument having an appropriate complimentary end effector.

Another application of the information gathered by such an ultrasound probe, or the like, is to collect preoperative data on the patient, at the surgical site, for example. Such preoperative data can then be used to determine a location of, for example, a stenosis, or blockage, or the like, in a blood vessel that is to be anastomosed during a heart bypass operation for example. The auxiliary information can then be overlaid on the "live" image of the surgical site to indicate to the surgeon where the surgeon should conduct the anastomosis. Conveniently, and as already described, markers or identifiers can then be attached to the location of the stenosis such that, should the displayed image be changed, such as, for example by moving the endoscope, the markers or identifiers remain in a registered condition with the stenosis so that the location of the stenosis remains clearly indicated in the displayed image.

Figure 15:
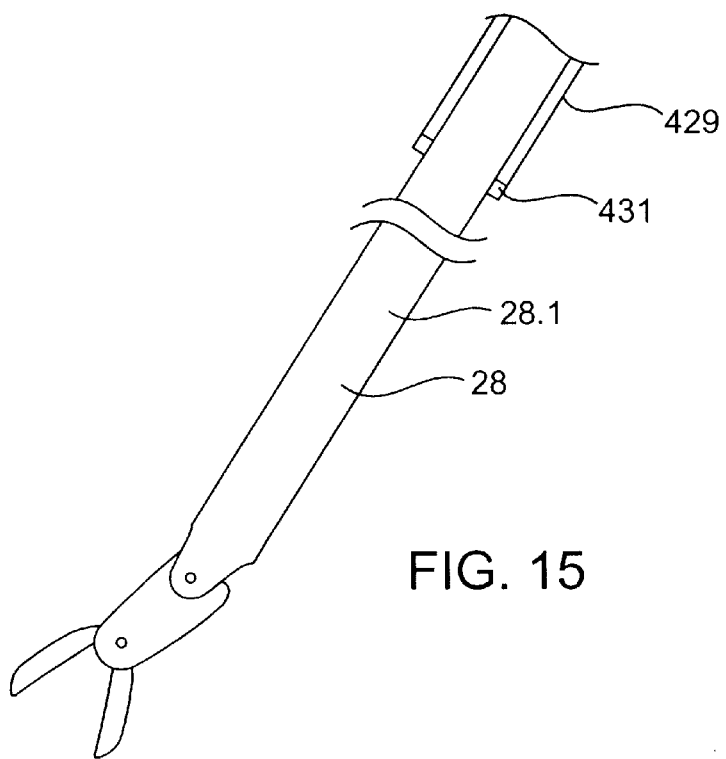
FIG. 15 shows a schematic side view of an image capturing device for capturing an image along a shaft of a surgical instrument of the system shown in FIG. 1, in accordance with the invention.

Another source of typically two-dimensional information will now be described with reference to FIG. 15 of the drawings. In FIG. 15, like reference numerals are used to designate similar parts unless otherwise stated. FIG. 15 shows a surgical instrument 28 extending through a cannula 429 mounted in an aperture extending into the patient body. At the end of the cannula 429, schematically indicated by reference numeral 431 is an image capture device. The image capture device can be in any appropriate form. For example, it can include optical fiber bundles, an annular image capturing ring, or a suitable microcamera, or the like. By means of the image capture device 431, an image extending along the length of the shaft 28.1 can be captured. This image can then be displayed selectively on the displayed image at the viewer. In this fashion, the surgeon can be provided with images from various vantage points which may provide him or her, with information otherwise not readily discernable. For example, by mounting such an image capture device directed along the shaft of the instrument, collisions between instrument shafts and the like can be avoided.

In accordance with another aspect of the invention, auxiliary information is provided to the surgeon to enable him or her to determine the orientation of the captured image displayed on the viewer relative to a frame of reference. For example, the auxiliary information can indicate to the surgeon which way is "up" relative to the displayed image or scene. Such auxiliary information can be presented in any appropriate manner, for example, by means of an icon, image, representation, or the like. One way of achieving this is by displaying a horizon "bar" or "line" in the image. Obviously, a horizon line will only be useful to a surgeon if the endoscope is not parallel to/coincident with the gravity vector. Otherwise, rotation of the endoscopic image will simply result in rotation of the image on a plane normal to gravity. Accordingly, when the "bar" is in a "horizontal" position in the image, the top of the displayed image is either up, or down. Preferably, the icon will include an image to enable the surgeon to distinguish between "up" and "down," such as a dot on the "up" side of the bar. This type of absolute registration of the horizon line, however, is not always necessary during surgery. If the image is changed, e.g., by rotating the endoscope, the bar is caused to rotate so as to indicate that "up" in the image no longer corresponds with gravitational "up". Therefore, the surgeon can be shown where he or she is with respect to an artificial "horizon" bar or line overlayed on the image captured by the endoscope.

This line or bar is preferably displayed to be perpendicular to the direction of gravity and perpendicular to the endoscope line of sight at its viewing end. This can be achieved by taking the cross product of the gravity vector expressed in a "world frame" with the optical (longitudinal) axis of the endoscope or camera rotation matrix, which is also expressed relative to the world frame. Therefore:

$$^{world}H = {}^{world}\begin{bmatrix} 0 \\ 0 \\ -1 \end{bmatrix} X^{world}z_{endoscope}$$

where H(world)=horizon vector in the world reference frame, and z(endoscope)=optical axis vector of endoscope.

This horizon vector, H(world), is preferably represented in the camera reference frame, T(endoscope)—the reference frame attached to the distal tip of the endoscope whose z—axis is its optical axis—by transposing the camera frame as follows:

$$^{endoscope}H = (^{world}T_{endoscop})^T \cdot {}^{world}H$$

where H(endoscope) is the horizon vector in the endoscope reference frame. In order to facilitate displaying the horizon line at any desired location on the image display screen, rather than with its origin at a particular image location such as the origin of the x and y axes of the camera/endoscope frame, only the angle relative to one of the x- and y-axes of the camera/endoscope frame—preferably the x-axis—need to be tracked. This angle can be determined by the geometric relationship between the x and y portions of H(endoscope) vector. Thus:

$$\text{Angle} = \arctan\left(\frac{^{endoscope}H(y)}{^{endoscope}H(x)}\right)$$

If it is desirable to distinguish between "up" and "down" in the image, calculation of the angle will also need to take into account whether either or both of the H(x) and H(y) values are positive or negative.

Figure 16A:
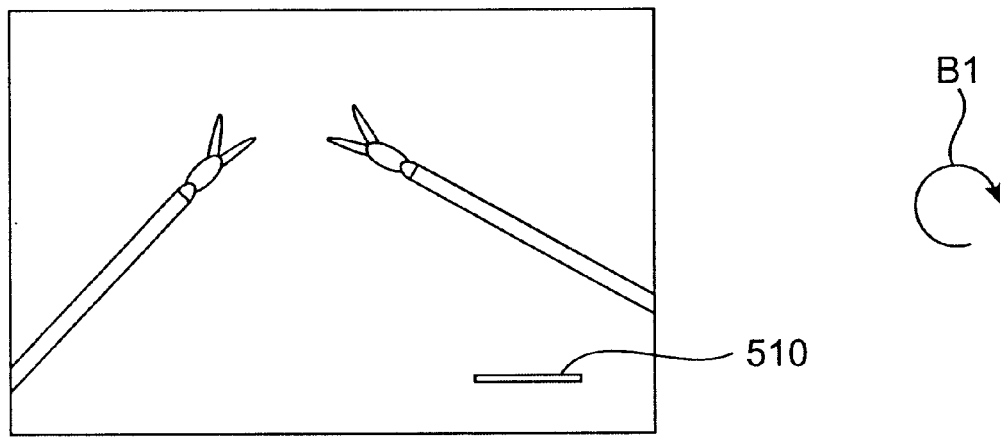
FIGS. 16A and 16B show schematic drawings indicating a rotational movement of a displayed image and a line or bar displayed in the image to indicate orientational position of a scene in the displayed image relative to a world reference frame.
Figure 16B:
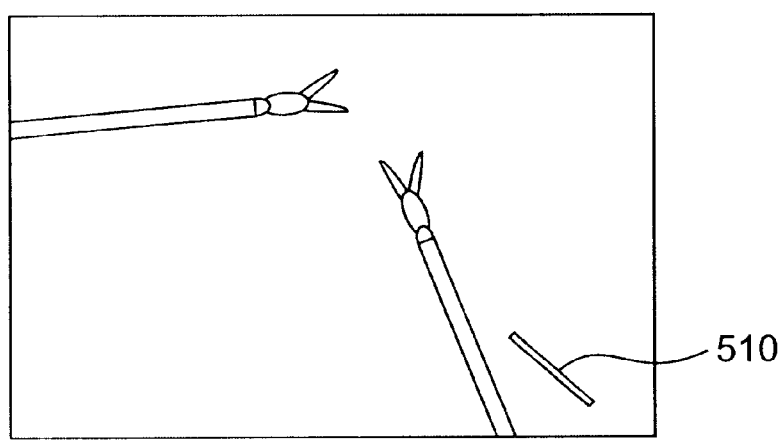
Figure 17A:
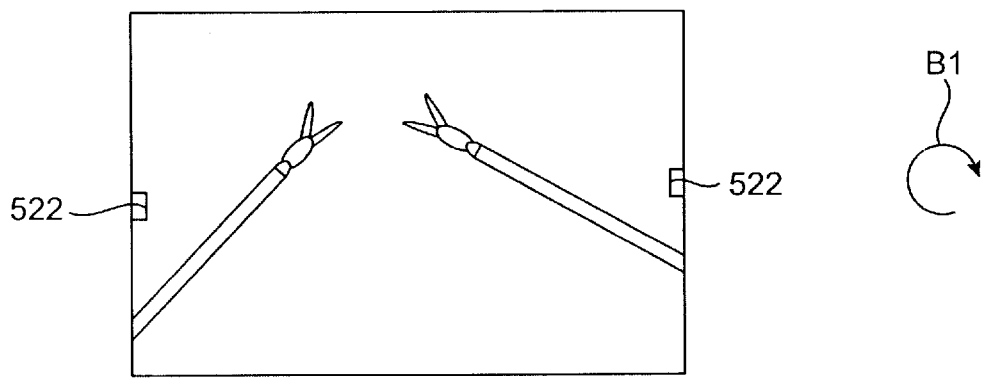
FIGS. 17A and 17B show schematic drawings indicating a rotational movement of a displayed image and opposed markers or indicators displayed in the image to indicate orientational position of a scene in the displayed image relative to a world reference frame.
Figure 17B:
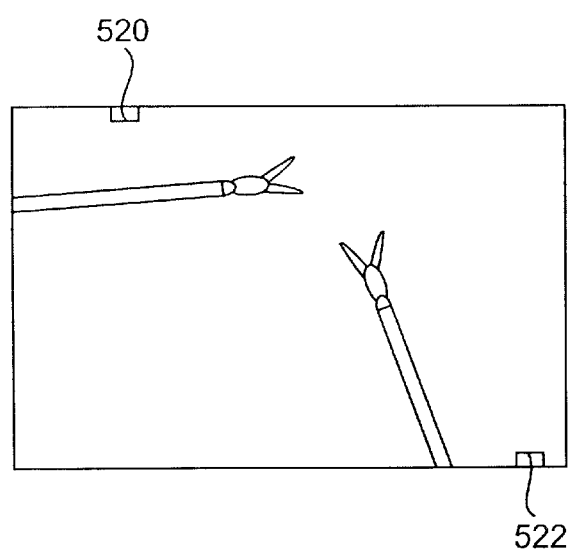

The artificial horizon or "bar" can then be displayed in the displayed image as indicated at 510 in FIG. 16A. If the endoscope is then rotated to rotate the displayed image in a clockwise direction as indicated by arrow B1, the line or bar 510 follows as indicated in FIG. 16B. Instead of a line or bar, an arrow corresponding with the direction of gravity can be used, in the manner of a virtual "plumb line" for example. Instead, and with reference to FIG. 17A, opposed indicators or cursors 520, 522 can be used. As the image is rotated clockwise, as indicated by arrow B2, for example, the markers are moved along with rotation of the image as indicated in FIG. 17B. The surgeon can then determine orientation with reference to an imaginary line extending between the markers 520, 522.

Another form of auxiliary information that can be displayed on the displayed image is one or more force indicators to indicate to the operator the degree of force applied between the fingers of the end effectors 60, for example. This can be achieved by measuring associated motor current for example, and can be in the form of a graph (such as a bar graph) associated with each of the end effectors and displayed on the image for the surgeon to see. The graph may include a variety of colors, with lighter forces indicated by both different colors as well as changes in magnitude of the graphic display. The graphs may indicate force direction as well as magnitude for example. A zeroing function can be included to negate effects of other forces on the end effectors such as if they contact tissue, or body walls, or the like.

While the above is a complete description of preferred embodiments of the invention, various alternatives, modifications and equivalents may be used. It should be evident that the present invention is equally applicable by making appropriate modifications to the embodiments described above. Therefore, the above description should not be taken as limiting the scope of the invention which is defined by the metes and bounds of the appended claims along with their fall scope of equivalents.

What is claimed is:

1. A method of performing a surgical procedure on a patient, the method comprising:

positioning a surgical work station of a robotically controlled surgical system and a patient on which a surgical procedure is to be performed in close proximity relative to each other;

directing a field of view of an image caprute device of the surgical work station at a surgical site on the patient, at which site the surgical procedure is to be performed;

introducing at least one robotically controlled surgical instrument on the surgical work station to the surgical site so that an end effector of the surgical instrument is within the field of view of the image capture device;

displaying an image of the surgical site and the end effector on a display area of an image display at an operator control station of the surgical system, the image display being operatively connected to the image capture device so as to display on the display area the image of the surgical site and the end effector captured by the image capture device;

permitting an operator of the surgical system to effect a manipulation of a linkage of a master control in three dimensions at the operator control station whilst viewing the image of the surgical site on the image display, the master control being operatively associated with the surgical instrument thereby to cause the end effector to move in response to the manipulation of the linkage of the master control so as to perform at least part of the surgical procedure on the patient at the surgical site;

operatively linking the image display to a source of selectively accessible auxiliary information related to the surgical procedure to be performed;

enabling the operator selecibely to access the source of auxiliary information from the operator control station so as to forward the auxiliary information to the image display;

causing the auxiliary information to be displayed across the display area of the image display in response to the operator selectively accessing the source of auxiliary information at the operator control station; and enabling the operator selectively to move the auxiliary information when displayed on the image display relative to the image of the surgical site displayed on the image display;

wherein the master control is operatively linked with the source of auxiliatry information, said enabling the operator selectively to access the source of auxiliary information comprising permitting toe operator selectively to disassociate the master control from the surgical instrument and to use the master control to access the source of auxiliary information in response to the manipulation of the linkage so as to enable the auxiliary information to be displayed on the display area of the image display.

2. A method of performing a surgical procedure as claimed in claim 1, wherein said enabling the operator selectively to access the source of auxiliary information comprises causing an icon to be displayed on the display area of the image display so that the operator can selectively access the auxiliary information by actuating the icon.

3. A method of performing a surgical procedure as claimed in claim 2, wherein the master control is operatively linked with the source of auxiliary information, said enabling the operator selectively to access the source of auxiliary information comprising permitting the operator selectively to disassociate the master control from the surgical instrument and to move the master control so as to guide a cursor displayed on the display area of the image display onto the icon so as to actuate the icon thereby to cause the auxiliary information to be displayed on the display area of the image display.

4. A method of performing a surgical procedure as claimed in any one of the preceding claims, wherein the master control is operatively linked to the auxiliary information when displayed on the display area of the image display so as to enable the operator to move the auxiliary information displayed on the image display relative to the image of the surgical site displayed on the image display by moving the master control.

5. A method of performing a surgical procedure as claimed in claim 4, wherein the master control is operatively linked to the auxiliary information, when displayed on the display area of the image display, through a transform of at least two dimensions to enable the auxiliary information to be displaced across the surface of the display area by changing the transform in response to movement of the master control.

6. A method of performing a surgical procedure as claimed in claim 1, wherein said causing the auxiliary information to be displayed on the image display comprises causing the auxiliary information to be displayed across a discrete area extending across part of the display area of the image display, the image of the surgical site being displayed across the rest of the display area.

7. A method of performing a surgical procedure as claimed in claim 6, wherein the image of the surgical site is caused to be displayed across a discrete area generally centrally disposed relative to the display area of the image display and the auxiliary information is caused to be displayed across a discrete area surrounding the area across which the image of the surgical site is displayed.

8. A method of performing a surgical procedure as claimed in claim 6, wherein the master control is operatively linked to the auxiliary information when selectively displayed on the display area of the image display so as to enable the operator to move the auxiliary information displayed on the image display relative to the image of the surgical site displayed on the image display by moving the master control.

9. A method of performing a surgical procedure as claimed in claim 8, wherein the dimensions of the discrete area across which the auxiliary information is displayed can be varied by manipulation of the master control.

10. A method of performing a surgical procedure as claimed in claim 6, wherein the auxiliary information is caused to be displayed within the bounds of a window extending across part of the display area of the image display, the image of the surgical site being displayed across the rest of the display area.

11. A method of performing a surgical procedure as claimed in claim 10, wherein the master control is operatively linked to the auxiliary information when selectively displayed on the display area of the image display so as to enable the operator to move the window in which the auxiliary information is displayed on the image display relative to the image of the surgical site displayed on the image display by moving the master control.

12. A method of performing a surgical procedure as claimed in claim 11, wherein the dimensions of the window can be changed relative to the image of the surgical site by manipulation of the master control.

13. A method of performing a surgical procedure as claimed in claim 1, wherein the auxiliary information is in the form of a three-dimensional model corresponding to the surgical site, said causing the auxiliary information to be displayed on the image display comprising causing the three-dimensional model to be mixed into the image of the surgical site so as to merge with the image of the surgical site.

14. A method of performing a surgical procedure as claimed in claim 13, wherein the master control is operatively linked to the auxiliary information when selectively displayed on the display area of the image display so as to enable the operator to move the three-dimensional model displayed on the image display relative to the image of the surgical site displayed on the image display by moving the master control.

15. A method of performing a surgical procedure as claimed in claim 14, wherein accessing the auxiliary information includes forwarding the information to the image display through a transform of at least three dimensions.

16. A method of performing a surgical procedure on a patient, the method comprising:
   manipulating a linkage of a master control in three dimensions whilst viewing a real time image of a surgical site on an image display;
   moving an end effector in response to the manipulation of the linkage of the master control, said end effector visible on said image display, so as to perform at least part of a surgical procedure at the surgical site;
   selectively accessing a source of auxiliary information in response to the manipulation of the linkage of the master control; and
   displaying the auxiliary information on the image display,
   wherein the master control is operatively associated with the end effector to cause the end effector to move in response to the manipulating of the master control, and wherein the selectively accessing the source of auxiliary information comprises disassociating the master control from the end effector.

17. A method as claimed in claim 16, further comprising causing the end effector to remain stationary while the master control is operatively disassociated therefrom.

18. A method as claimed in claim 16, further comprising causing a cursor to be generated on the image display so that the master control can be selectively used to access the source of auxiliary information.

19. A method as claimed in claim 18, wherein the source of auxiliary information is represented by an icon displayed on the image display, said accessing the source of auxiliary information comprising moving the cursor across the image display in response to manipulation of the master control and actuating the icon by at least having the position of the cursor correspond with the position of the icon.

20. A method as claimed in claim 19, wherein actuating the icon comprises manipulation of the master control.

21. A method as claimed in claim 19, wherein the auxiliary information is caused to be displayed on the image display in response to actuating the icon.

22. A method as claimed in claim 16, wherein causing the auxiliary information to be displayed on the image display comprises displaying the auxiliary information in a discrete window on the image display.

23. A method as claimed in claim 22, which further comprises varying the position of the discrete window across the image display.

24. A method as claimed in claim 23, wherein varying the position of the discrete window across the image display comprises manipulating the master control.

25. A method as claimed in claim 22, which further comprises varying the dimensions of the discrete window on the image display.

26. A method as claimed in claim 25, wherein varying the dimensions of the discrete window on the image display comprises manipulating the master control.

27. A method as claimed in claim 22, which further comprises varying the orientation of the discrete window on the image display.

28. A method as claimed in claim 27, wherein varying the orientation of the discrete window on the image display comprises manipulating the master control.

29. A method as claimed in claim 1 or claim 16, wherein the auxiliary information at the source of auxiliary information is selected from the group consisting of any one or more of a CAT scan image, an MRI image, an X-ray image, and an ultrasonic image.

30. A method as claimed in claim 1 or claim 16, wherein the auxiliary information at the source of auxiliary information is selected from the group consisting of any one or more of an ECG signal, a blood pressure signal, and a heartbeat signal.

31. A method as claimed in claim 1 or claim 16, wherein the auxiliary information at the source of auxiliary information is selected from the group consisting of any one or more of a warning message, a clock indicating time, an e-mail service, a temperature reading, oxygen levels in a patient's blood, and a remote computer.

32. A method as claimed in claim 1 or claim 16, wherein the auxiliary information at the source of auxiliary information is selected from the group consisting of any one or more of a streaming video corresponding to a surgical procedure to be performed, generic anatomical images, and patient specific anatomical images.

33. A method as claimed in claim 1 or claim 16, wherein the auxiliary information at the source of auxiliary information is selected from the group consisting of any one or more of a three dimensional model, raw volumetric images, a computer generated model, and a computer generated image.

34. A method as claimed in claim 1 or claim 16, wherein the auxiliary information at the source of auxiliary information is selected from the group consisting of any one or both of images of surgical instrument shaft locations and images of entry port locations through which surgical instruments extend.

35. A method as claimed in claim 16, wherein the auxiliary information is in the form of an auxiliary image corresponding to the surgical site at which it is desired to perform the surgical procedure, said causing the auxiliary information to be displayed on the image display comprising at least generally merging the auxiliary image with the image of the surgical site so that the images are superimposed and are both visible on the image display.

36. A method as claimed in claim 35, further comprising capturing the auxiliary image corresponding to the surgical site by means of any one of the methods selected from the group consisting of X-ray, MRI, ultrasound and CAT scan.

37. A method as claimed in claim 35, which comprises capturing the auxiliary image prior to performing the surgical procedure at the surgical site and loading the auxiliary image into a memory thereby to create the source of auxiliary information.

38. A method as claimed in claim 35, in which the auxiliary image is in the form of a real-time image captured during the surgical procedure, said at least generally merging the auxiliary image with the image of the surgical site comprising at least generally merging the real-time auxiliary image with the image of the surgical site.

39. A method as claimed in claim 35, further comprising bringing the auxiliary image at least generally into registration with the image of the surgical site.

40. A method as claimed in claim 39, wherein said bringing the auxiliary image at least generally into registration with the image of the surgical site comprises manipulating the master control.

41. A method as claimed in claim 39, wherein said bringing the auxiliary image at least generally into registration with the image of the surgical site comprises causing the auxiliary image automatically to be brought into registration with the image of the surgical site.

42. A method as claimed in claim 39, wherein said bringing the auxiliary image into registration with the image of the surgical site comprises manipulating the master control to bring the auxiliary image generally into register with the surgical site and then causing the auxiliary image to be brought into more accurate registration without further movement of the master control.

43. A method as claimed in claim 16, wherein the auxiliary information comprises an image of the surgical site which is more panoramic than the real time image of the surgical site, said displaying the auxiliary image on the image display comprising displaying the auxiliary information so as to extend around a periphery of the real-time image of the surgical site.

44. A method as claimed in claim 16, wherein the auxiliary information comprises an image corresponding to a constraint, or barrier, the method further comprising at least generally merging the image of the constraint with the image of the surgical site so that the images are superimposed with each other, the image of the constraint being arranged to indicate that movement of the end effector through the image of the constraint is either to be avoided or not possible.

45. A method as claimed in claim 44, which further comprises moving the image of the constraint relative to the image of the surgical site.

46. A method as claimed in claim 45, wherein the master control can be selectively operatively associated with the image of the constraint, said moving the image of the constraint relative to the image of the surgical site comprising manipulating the master control to place the image of the constraint relative to the image of the surgical site in a location corresponding to a position beyond which the surgeon desires not to move any surgical tool.

47. A method as claimed in claim 44, wherein the constraint has a predetermined shape selected from the group consisting of a virtual wall, a virtual shape corresponding to part of the surface of a sphere and a virtual multi-planar shape.

48. A method as claimed in claim 16, wherein the real-time image of the surgical site is captured by an image capture device, the source of auxiliary information being in the form of another image capture device positioned to capture an image related to the surgical procedure from a vantage point different to a vantage point from which the real-time image of the surgical site is captured, the method further comprising capturing and displaying an auxiliary image from the other image capture device on the image display together with the image of the real-time surgical site.

49. A method as claimed in claim 48, wherein capturing the auxiliary image comprises capturing an auxiliary image directed along a shaft on which the end effector is mounted.

50. A method as claimed in claim 16, wherein the auxiliary information comprises a horizon bar indicating to the surgeon the general orientation of the image relative to gravity.

51. A method for preparing for or performing a robotic surgical procedure at a surgical site on a patient, the method comprising:

displaying information relevant to the surgical procedure on an image display of the robotic surgical system;

manipulating a linkage of a master control of the robotic surgical system in three dimensions while viewing the image display;

moving an end effector of the robotic surgical system in response to the manipulation of the linkage of the master control so as to prepare for or perform at least part of a surgical procedure at the surgical site when the robotic surgical system is in a first operating mode; and changing the displayed information on the image display of the robotic surgical system in response to the manipulation of the linkage of the master control when the robotic surgical system is in a second operating mode.

52. The method of claim 51, further comprising capturing an image of the surgical site with an image capture device and displaying the captured image on the image display, wherein the displayed information comprises auxiliary information, and wherein the changing step comprises moving the auxiliary information with at least two degrees of freedom across the image display.

53. A system for performing a surgical procedure at a surgical site on a patient, the system comprising:

a master having an input device, a linkage of the input device configured for manipulation by a hand of a system operator so as to define a manipulation in three dimensions;

a surgical end effector;

an image display for displaying information relevant to the surgical procedure; and a processor coupling the input device to the end effector and the image display, the processor having first and second operating modes, the processor in the first operating mode effecting movement of the end effector in response to the manipulation of the input device, the processor in the second operating mode changing the displayed information in response to the manipulation of the input device.

* * * * *